United States Patent
Edderkaoui et al.

(10) Patent No.: US 10,836,735 B2
(45) Date of Patent: Nov. 17, 2020

(54) COMPOSITIONS AND METHODS FOR TREATING CANCERS

(71) Applicant: CEDARS-SINAI MEDICAL CENTER, Los Angeles, CA (US)

(72) Inventors: Mouad Edderkaoui, Los Angeles, CA (US); Ramachandran Murali, Swarthmore, PA (US); Stephen Pandol, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 16/292,011

(22) Filed: Mar. 4, 2019

(65) Prior Publication Data

US 2019/0194152 A1    Jun. 27, 2019

Related U.S. Application Data

(60) Continuation of application No. 16/012,536, filed on Jun. 19, 2018, now Pat. No. 10,266,505, which is a division of application No. 15/317,559, filed as application No. PCT/US2015/035659 on Jun. 12, 2015, now Pat. No. 10,029,997.

(60) Provisional application No. 62/011,413, filed on Jun. 12, 2014.

(51) Int. Cl.
| | |
|---|---|
| *C07D 285/08* | (2006.01) |
| *C07D 271/10* | (2006.01) |
| *C07D 271/107* | (2006.01) |
| *A61K 31/433* | (2006.01) |
| *A61K 45/06* | (2006.01) |
| *A61K 31/167* | (2006.01) |
| *A61K 31/4245* | (2006.01) |
| *C07D 271/113* | (2006.01) |

(52) U.S. Cl.
CPC .......... *C07D 285/08* (2013.01); *A61K 31/167* (2013.01); *A61K 31/4245* (2013.01); *A61K 31/433* (2013.01); *A61K 45/06* (2013.01); *C07D 271/10* (2013.01); *C07D 271/107* (2013.01); *C07D 271/113* (2013.01)

(58) Field of Classification Search
CPC .................................................. C07D 285/08
See application file for complete search history.

(56) References Cited

U.S. PATENT DOCUMENTS

| | | | |
|---|---|---|---|
| 3,711,492 A * | 1/1973 | Rohr et al. ........... | C07D 285/08 548/130 |
| 6,689,794 B2 | 2/2004 | Freskos et al. | |
| 7,498,298 B2 | 3/2009 | Doronina et al. | |
| 7,812,016 B2 | 10/2010 | Johns | |
| 8,158,661 B2 | 4/2012 | Medina et al. | |
| 9,489,324 B2 | 11/2016 | Sakurai et al. | |
| 10,029,997 B2 | 7/2018 | Edderkaoui | |
| 2005/0038113 A1 | 2/2005 | Groner et al. | |
| 2006/0069097 A1 | 3/2006 | Dickerson et al. | |
| 2009/0081318 A1 | 3/2009 | Gelbard et al. | |
| 2009/0142337 A1 | 6/2009 | Squires | |
| 2009/0304663 A1 | 12/2009 | Kypta | |
| 2010/0069381 A1 | 3/2010 | Itoh et al. | |
| 2012/0015942 A1 | 1/2012 | Calderwood et al. | |
| 2018/0297965 A1 | 10/2018 | Edderkaoui et al. | |

FOREIGN PATENT DOCUMENTS

| | | |
|---|---|---|
| WO | WO-0059874 A1 | 10/2000 |
| WO | WO-2005075469 A1 | 8/2005 |
| WO | WO-2008132153 A1 | 11/2008 |
| WO | WO-2012012320 A1 | 1/2012 |
| WO | WO-2013007663 A1 | 1/2013 |
| WO | WO-2015192078 A1 | 12/2015 |

OTHER PUBLICATIONS

Arnold et al. The Histone Deacetylase Inhibitor Suberoylanilide Hydroxamic Acid Induces Growth Inhibition and Enhances Gemcitabine-Induced Cell Death in Pancreatic Cancer. Clin Cancer Res (2007) 13(1):18-26.
Chao et al. A Novel Magnetic Nanoparticle Drug Carrier for Enhanced Cancer Chemotherapy. PLoS One (2012). 7(10):e40388, 7 pages.
Chemical Abstract Registry No. 1030143-96-4, Indexed in the Registry file on STN CAS Online Jun. 24, 2008, 1 page.
Chemical Abstract Registry No. 1241105-71-4, Indexed in the Registry file on STN CAS Online Sep. 15, 2010, 1 page.
Chemical Abstracts Registry No. 1061794-10-2, indexed in the Registry file on STN CAS Online on Oct. 15, 2008, 1 page.
Chemical Abstracts Registry No. 1026513-33-6, indexed in the Registry file on STN CAS Online on Jun. 8, 2008.
Cheng et al. Novel Agents for the Treatment of Pancreatic Adenocarcinoma. J Pancreas (Online) 12(4):334-338 (2011).
Chinese Patent Application No. 201580042796.X Office Action dated Nov. 13, 2018.
Choi et al. Protease-Activated Drug Development. Theranostics (2012). 2(2):156-178.
European Patent Application No. 15806839.5 extended European Search Report dated Nov. 22, 2017.
European Patent Application No. 15806839.5 European Office Action dated Jan. 16, 2019.

(Continued)

*Primary Examiner* — Laura L Stockton
(74) *Attorney, Agent, or Firm* — Wilson Sonsini Goodrich & Rosati

(57) ABSTRACT

The invention describes compounds that inhibit both HDAC and GSK3β (i.e., HDAC/GSK3β dual inhibitors). The invention further describes compositions containing these HDAC/GSK3β dual inhibitors, as well as methods and kits using these HDAC/GSK3β dual inhibitors to treat various medical conditions. The invention also provides methods and kits using a HDAC inhibitor and a GSK3β to treat various medical conditions, and compositions containing a HDAC inhibitor and a GSK3β. Medical conditions treatable with various embodiments of the invention include but are not limited to cancers and tumors.

13 Claims, 12 Drawing Sheets

(56) References Cited

OTHER PUBLICATIONS

Fedi et al., Italian Patent No. IT-1362200-B1, Abstract of Italian Document provided by the USPTO, patent published Jun. 19, 2009, 6 pages.
Golub et al., Molecular classification of cancer: Class discovery and class prediction by gene expression monitoring. Science, 286:531-537, 1999.
Italian Patent No. 1362200-B1, English translation, "Formulations That Contemplate." 18 pages, 2009.
Khanfar et al., Discovery of novel GSK-3beta inhibitors with potent in vitro and in vivo activities and excellent brain permeability using combined ligand- and structure-based virtual screening. J. Med.Chem., 53:8534-8545, 2010.
Koutsounas et al. Current evidence for histone deacetylase inhibitors in pancreatic cancer. World J Gastroenterol (2013). 19(6):813-828.
Kramer et al. Small-Molecule Inhibitors of GSK-3: Structural Insights and Their Application to Alzheimer's Disease Models. Int J Alzheimers Disease 2012:381029 (2012).
Kumagai et al. Histone deacetylase inhibitor, suberoylanilide hydroxamic acid (Vorinostat, SAHA) profoundly inhibits the growth of human pancreatic cancer cells. Int J Cancer (2007). 121(3):656-665.
Marchand et al. Inhibition of glycogen synthase kinase-3 activity triggers an apoptotic response in pancreatic cancer cells through JNK-dependent mechanisms. Carcinogenesis (2012). 0(0): pp. 1-9.
Naito et al. Glycogen Synthase Kinase-3beta: A Prognostic Marker and a Potential Therapeutic Target in Human Bladder. Cancer. Clin Cancer Res (2010). 16(21): 9 pages. pp. OF1-OF9.
Ouaissi et al. Rationale for Possible Targeting of Histone Deacetylase Signaling in Cancer Diseases with a Special Reference to Pancreatic Cancer. Journal of Biomedicine and Biotechnology 2011:315939 (8 pages) (2011).
PCT/US2015/035659 International Search Report and Written Opinion dated Sep. 15, 2015.
Rajak et al., 2,5-Disubstituted-1,3,4-oxadiazoles/thiadiazole as surface recognition moiety: Design and synthesis of novel hydroxamic acid based histone deacetylase inhibitors. Bioorganic & Medicinal Chemistry Letters, 21:5735-5738, 2011.
U.S. Appl. No. 15/317,559 Office Action dated Feb. 16, 2018.
U.S. Appl. No. 15/317,559 Office Action dated Oct. 5, 2017.
U.S. Appl. No. 16/012,536 Office Action dated Aug. 23, 2018.
Valente et al., 1,3,4-Oxadiazole-containing histone deacetylase inhibitors: Anticancer activities in cancer cells. Journal of Medicinal Chemistry, 57:6259-6265, 2014.
Wilson et al., Cathepsin G Enhances Mammary Tumor-Induced Osteolysis by Generating Soluble Receptor Activator of Nuclear Factor-KB Ligand. Cancer Res (2008). 68(14):5803-5811.
Wilson et al. Cathepsin G-Mediated Activation of Pro-Matrix Metalloproteinase 9 at the Tumor-Bone Interface Promotes Transforming Growth Factor-beta Signaling and Bone Destruction. Mol Cancer REs (2009). 7(8):1224-1233.
Yang et al. Potential of magnetic nanoparticles for targeted drug delivery. Nanotechnology, Science and Applications. (2012). 5:73-86.

\* cited by examiner

| Functional Group | Activation / Coupling |
|---|---|
| SiMAG-Amine<br>◯- Si-(CH$_2$)$_3$-NH$_2$ | Carbodiimide method<br>Mannich reaction |
| SiMAG-Carboxyl<br>◯- Si-(CH$_2$)$_3$-COOH | Carbodiimide method |

COMPOSITIONS AND METHODS FOR TREATING CANCERS

CROSS-REFERENCE TO RELATED APPLICATIONS

This application is a continuation of U.S. application Ser. No. 16/012,536 filed Jun. 19, 2018, now issued as U.S. Pat. No. 10,266,505 on Apr. 23, 2019, which is a divisional of U.S. application Ser. No. 15/317,559, filed Dec. 9, 2016, now issued as U.S. Pat. No. 10,029,997 on Jul. 24, 2018, which is a U.S. National Stage entry of International Application No. PCT/US2015/035659 filed Jun. 12, 2015 which claims the benefit under 35 U.S.C. § 119(e) of the U.S. Provisional Application No. 62/011,413, filed Jun. 12, 2014, the content of which is incorporated herein by reference in its entirety.

STATEMENT REGARDING FEDERALLY-SPONSORED RESEARCH

This invention was made with government support under Grant Nos. AA019996 and CA163200 awarded by the National Institutes of Health (NIH). The government has certain rights in the invention.

FIELD OF THE INVENTION

The invention relates to compounds, compositions, methods and kits for treating a medical condition. The condition includes but is not limited to a cancer or tumor.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Strong correlation exists between over expression of glycogen synthase kinase 3 beta (GSK3β) and cancer progression in humans. Activation of GSK3β up-regulates proliferation and increases resistance to apoptosis in cancer cells through activation of pro-survival pathways including the NF-κB pathway. These observations suggest that inhibition of GSK3β is a potential treatment strategy for many cancers. However, while GSK3β inhibitors decrease cancer cell proliferation, they stimulate the conversion of cancer cells to ones that are more likely to invade surrounding normal tissue and metastasize. This conversion to an invasive metastatic state is called epithelial mesenchymal transition (EMT). EMT is also associated with cancer cells that are more resistant to therapies because of the cancer cell converting to a cancer stem cell (or stemness).

This invention demonstrates that inhibitors of the enzyme histone deacetylase (HDAC) prevent EMT and enhance the anti-tumor effect of inhibitors of GSK3β, and provides compounds, compositions, methods and kits for treating various conditions including but not limited to cancers and tumors.

SUMMARY OF THE INVENTION

Various embodiments of the present invention provide a compound that inhibits both HDAC and GSK3β (i.e., a dual inhibitor of HDAC and GSK3β). In some embodiments, the dual inhibitor compound is represented by (V):

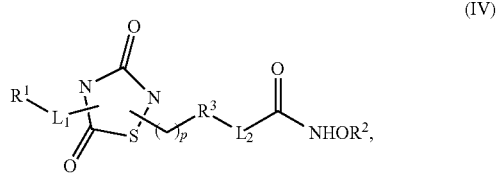

(IV)

wherein: $L_1$ and $L_2$ are independently a linker; $R^1$ is an aromatic moiety, alkyl, acyl, cyclyl or heterocyclyl, each of which can be optionally substituted; $R^2$ is hydrogen, lower alkyl, cyclyl, heterocyclyl, aryl, or heteroaryl, each of which can be optionally substituted; $R^3$ is absent or an aromatic moiety, which can be optionally substituted; p is 0, 1, 2, 3, 4, 5, 6, 7, 8, 9, or 10; and wherein one. $R^1$-$L_1$- is linked to one nitorgen of the thiadiazolidine ring and —$(CH_2)_p$—$R^3$-$L_2$-C(O)NHOR$^2$ is linked to the other nitorgen of the thiadiazolidine ring.

In some other embodiments, the dual inhibitor compound is represented by Formula (V):

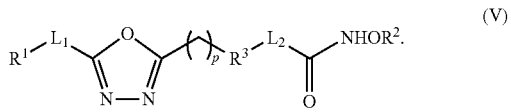

(V)

wherein: $L_1$ and $L_2$ are independently a linker; $R^1$ is an aromatic moiety, alkyl, acyl, cyclyl or heterocyclyl, each of which can be optionally substituted; $R^2$ is hydrogen, lower alkyl, cyclyl, heterocyclyl, aryl, or heteroaryl, each of which can be optionally substituted; $R^3$ is absent or an aromatic moiety, which can be optionally substituted; and p is 0, 1, 2, 3, 4, 5, 6, 7, 8, 9, or 10.

Various embodiments of the present invention provide a composition that consists of or consists essentially of or comprises a dual inhibitor of HDAC and GSK3β. In various further embodiments, the dual inhibitor is attached to a cleavable enzyme substrate. In some embodiments, the cleavable enzyme substrate is attached to a particle, such as a magnetic particle.

Various embodiments of the present invention provide a method of treating, preventing, reducing the likelihood of having, reducing the severity of and/or slowing the progression of a condition in a subject. The method consists of or consists essentially of or comprises: administering a therapeutically effective amount of the dual inhibitor of HDAC and GSK3β to the subject, thereby treating, preventing, reducing the likelihood of having, reducing the severity of and/or slowing the progression of the condition in the subject. In various embodiments, the method further comprises providing the dual inhibitor.

In various embodiments, the method can further comprise administration or treatment with one or more additional anti-cancer therapies in addition to administering the dual inhibitor. In some such embodiments, the additional anti-cancer therapy comprises surgery, radiation therapy, biotherapy, immunotherapy, chemotherapy, or any combination thereof.

Some embodiments of the method can further comprise administration or treatment with one or more anti-cancer therapeutic agents in addition to administering the dual inhibitor. In some such embodiments, the anti-cancer therapeutic agent can be a chemotherapeutic agent, a growth inhibitor agent, an anti-angiogenesis agent, a cytotoxic agent, an anti-hormonal agent, a prodrug, a cytokine, or any combinations thereof. In some embodiments, the method further comprises administering a chemotherapeutic agent to the subject.

In still further embodiments, the dual inhibitor is attached to a cleavable enzyme substrate and the cleavable enzyme substrate is attached to a magnetic particle, and the method further comprises using a magnetic field to guide the dual inhibitor to a cancer or tumor.

Various embodiments of the present invention provide a kit for treating, preventing, reducing the severity of and/or slowing the progression of a condition in a subject. The kit consists of or consists essentially of or comprises: a quantity of a dual inhibitor of HDAC and GSK3β; and instructions for using the dual inhibitor to treat, prevent, reduce the likelihood of having, reduce the severity of and/or slow the progression of the condition in the subject. In various further embodiments, the dual inhibitor is attached to a cleavable enzyme substrate and the cleavable enzyme substrate is attached to a magnetic particle.

Various embodiments of the present invention provide a composition that consists of or consists essentially of or comprises a HDAC inhibitor and a GSK3β inhibitor. In various further embodiments, the HDAC inhibitor and/or the GSK3β inhibitor are attached to a cleavable enzyme substrate and the cleavable enzyme substrate is attached to a magnetic particle.

Various embodiments of the present invention provide a method of treating, preventing, reducing the likelihood of having, reducing the severity of and/or slowing the progression of a condition in a subject. The method consists of or consists essentially of or comprises: administering a therapeutically effective amount of an HDAC inhibitor and a GSK3β inhibitor to the subject, thereby treating, preventing, reducing the likelihood of having, reducing the severity of and/or slowing the progression of the condition in the subject. In various embodiments, the method further comprises providing the HDAC inhibitor and/or the GSK3β inhibitor.

In various embodiments, the method can further comprise administration or treatment with one or more additional anti-cancer therapies in addition to the HDAC inhibitor and the GSK3β inhibitor. In some such embodiments, the additional anti-cancer therapy comprises surgery, radiation therapy, biotherapy, immunotherapy, chemotherapy, or any combination thereof.

Some embodiments of the method can further comprise administration or treatment with one or more anti-cancer therapeutic agents in addition to the HDAC inhibitor and the GSK3β inhibitor. In some such embodiments, the anti-cancer therapeutic agent can be a chemotherapeutic agent, a growth inhibitor agent, an anti-angiogenesis agent, a cytotoxic agent, an anti-hormonal agent, a prodrug, a cytokine, or any combinations thereof. In some embodiments, the method further comprises administering a chemotherapeutic agent to the subject.

In still further embodiments, the HDAC inhibitor and/or the GSK3β inhibitor are attached to a cleavable enzyme substrate and the cleavable enzyme substrate is attached to a magnetic particle, and the method further comprises using a magnetic field to guide the HDAC inhibitor and/or the GSK3β inhibitor to a cancer or tumor.

Various embodiments of the present invention provide a kit for treating, preventing, reducing the severity of and/or slowing the progression of a condition in a subject. The kit consists of or consists essentially of or comprises: a quantity of a HDAC inhibitor; a quantity of a GSK3β inhibitor; and instructions for using the HDAC inhibitor and the GSK3β inhibitor to treat, prevent, reduce the likelihood of having, reduce the severity of and/or slow the progression of the condition in the subject. In various further embodiments, the HDAC inhibitor and/or the GSK3β inhibitor are attached to a cleavable enzyme substrate and the cleavable enzyme substrate is attached to a magnetic particle.

Various compounds, compositions, methods and kits of the present invention find utility in the treatment of various conditions, including but not limited to cancers and tumors.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
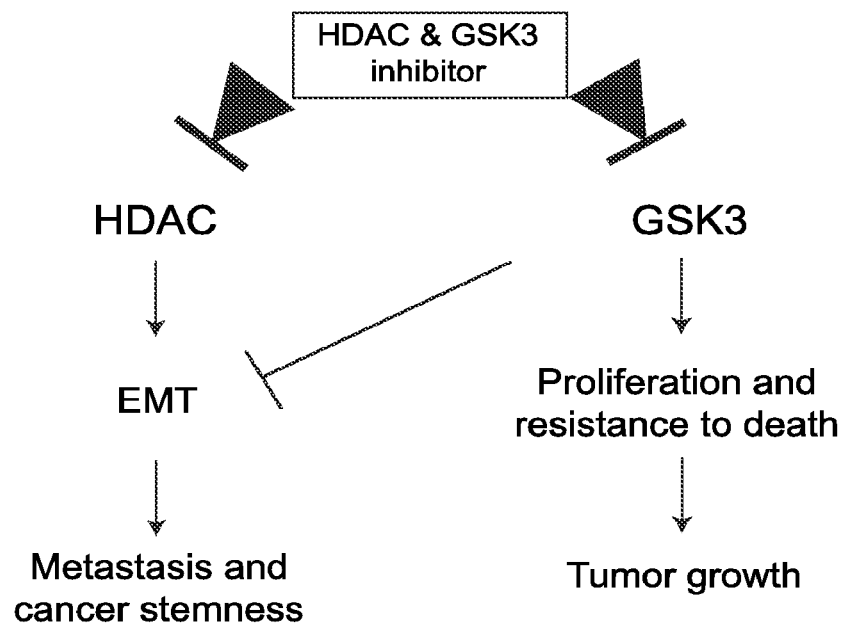
FIG. 1 depicts, in accordance with various embodiments of the invention, the inventors' novel strategy to inhibit cancer growth, metastasis and resistance to treatment.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, N.Y. 2006); Smith, March's Advanced Organic Chemistry Reactions, Mechanisms and Structure 7$^{th}$ ed., J. Wiley & Sons (New York, N.Y. 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul. 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of cancer or tumor, delay or slowing of cancer or tumor, and amelioration or palliation of symptoms associated with cancer or tumor.

"Conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Melanoma is an invasive form of skin tumor. As used herein, the term "carcinoma" refers to a cancer arising from epithelial cells.

Examples of cancer include, but are not limited to, nervous system tumor, brain tumor, nerve sheath tumor, breast cancer, colon cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, carcinoma, melanoma, head and neck cancer, brain cancer, and prostate cancer, including but not limited to androgen-dependent prostate cancer and androgen-independent prostate cancer. Examples of brain tumor include, but are not limited to, benign brain tumor, malignant brain tumor, primary brain tumor, secondary brain tumor, metastatic brain tumor, glioma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., cancer or tumor) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "anti-cancer therapy" refers to a therapy useful in treating cancer. Examples of anti-cancer therapeutic agents include, but are limited to, e.g., surgery, radiation therapy, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin™), anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the embodiments described herein.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

As used herein, a "chemotherapeutic agent" is a chemical compound useful in the treatment of cancer. Examples of chemotherapeutic agents include, but are not limited to, alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™, polysaccharide complex (JHS Natural Products, Eugene, Oreg.); razoxane; rhizoxin; sizofuran; spirogermanium; tenuazonic acid; triaziquone; 2,2',2"-trichlorotriethylamine;

trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™, paclitaxel (Bristol-Myers Squibb Oncology, Princeton, N.J.), ABRAXANE™, Cremophor-free, albumin-engineered nanoparticle formulation of paclitaxel (American Pharmaceutical Partners, Schaumberg, Ill.), and TAXOTERE™, doxetaxel (Rhone-Poulenc Rorer, Antony, France); chloranbucil; GEMZAR™ gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE.® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva™.)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

In some embodiments, the chemotherapeutic agent is selected from the group consisting of Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabinc, Floxuridine, Fludarabinc, Pentostatin, Mitomycin, ixabepilone, Estramustine, prednisone, methylprednisolone, dexamethasone or a combination thereof.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorclaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and —II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), TAXOL™, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

The term "statistically significant" or "significantly" refers to statistical evidence that there is a difference. It is defined as the probability of making a decision to reject the null hypothesis when the null hypothesis is actually true. The decision is often made using the p-value.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadicne, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S. The term "alkyl" includes heteroalkyl.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls.

In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes C, and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=CH CH=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3cjpyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1, 5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, $NR^N$—, —$N^+(O^-)$═, —O—, —S— or —$S(O)_2$—, —$OS(O)_2$—, and —SS—, wherein $R^N$ is H or a further substituent.

The term "hydroxy" means the radical —OH.

The term "imine derivative" means a derivative comprising the moiety C(NR)—, wherein R comprises a hydrogen or carbon atom alpha to the nitrogen.

The term "nitro" means the radical —$NO_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl, alkenyl, alkynyl, aryl, heteroaryl, cyclyl or heterocyclyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-cyclyl, —O-heterocyclyl, —O-aryl and —O-heteroaryl. The terms "alkoxyl" or "alkoxy" includes aroxy and aryloxy. Aroxy can be represented by O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. The term "alkylthio" further encompasses arylthio. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl) or -(alkyl)-(heteroaryl), such as benzyl (i.e., —CH$_2$phenyl), —CH$_2$-pyrindinyl, and the like.

The term "arylalkyloxy" means —O-(alkyl)-(aryl) or —O-(alkyl)-(heteroaryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl), such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —NHCH$_2$— cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-methylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

In some embodiments, the compounds described herein can be in the form of a prodrug. The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999);

Waller et al., "Prodrugs", *Br. J. Clin. Pharmac.* 28: 497-507 (1989), content of all of which are herein incorporated by reference in its entirety.

The term "protected derivatives" means derivatives of compounds described herein in which a reactive site or sites are blocked with protecting groups. Protected derivatives are useful in the preparation of compounds or in themselves can be active. A comprehensive list of suitable protecting groups can be found in T. W. Greene, *Protecting Groups in Organic Synthesis*, 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100x*F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

As used herein, the term "linker" means an organic moiety that connects two parts of a compound. Linkers typically comprise a direct bond or an atom such as oxygen or sulfur, a unit such as $NR^4$, C(O), C(O)NH, C(O)O, NHC(O)O, OC(O)O, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkyl aryl alkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $NR^4$, C(O), C(O)NH, C(O)O, NHC(O)O, OC(O)O, $SO_2NH$, cleavable linking group, substituted or unsubstituted aryl, substituted or unsubstituted heteroaryl, substituted or unsubstituted heterocyclic; where $R^4$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. A linking group cleavable by an enzyme can be an enzyme substrate that undergoes cleavage by the enzyme. Such a substrate is also referred to as cleavable enzyme substrate herein. The type of cleavable linking group incorporated into a linker can depend on the cell to be targeted. Linkers that contain peptide bonds can be used when targeting cell types rich in peptidases.

Figures 11, 12:
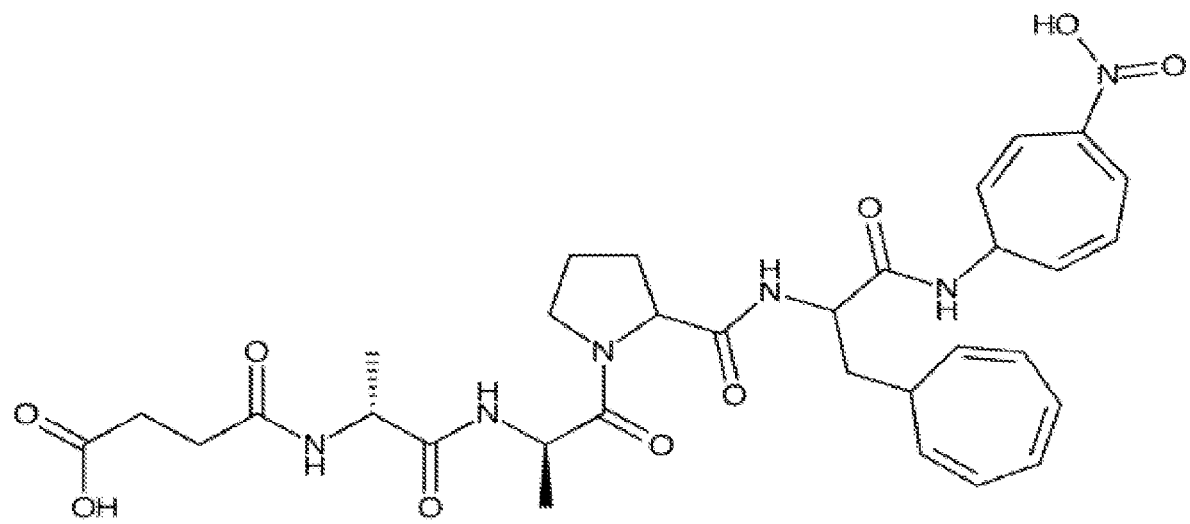
FIG. 11 depicts, in accordance with various embodiments of the invention, one non-limiting example of protease moiety for pancreatic cancer: Cathepsin G substrate.
FIG. 12 depicts, in accordance with various embodiments of the invention, non-limiting example of nanomaterials for pancreatic cancer: siMAG. As shown, the HDAC inhibitor, the GSK3β inhibitor, and/or the dual inhibitor can be conjugated to the si-MAG particles using the well-known carbodiimide coupling method or the Mannich reaction.

In some embodiments, the linker can include a cleavable linking group that is cleavable by Cathepsin G. An exemplary molecule that is cleaved by Cathepsin G is shown in FIG. 11.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.5, 6.0, 5.5, 5.0, or lower), or by agents such as enzymes that can act as a general acid.

Linkers according to the present invention also include prodrug moieties and nanoparticles. For a non-limiting example, a prodrug moiety can be a linker that is susceptible to "cleavage" to produce active form of the drug. More information may be found in Bundgard (1985, Design of Prodrugs, pp. 7-9, 21-24, Elsevier, Amsterdam) and Silverman (1992, the Organic Chemistry of Drug Design and Drug Action, pp. 352-401, Academic Press, San Diego, Calif.), which are incorporated herein by reference in their entirety as though fully set forth.

In some embodiments, the cleavable linking group is cleavable by an enzyme found in higher amounts in a cancer cell or tumor as compared to the amount in non-cancer or normal cells. For example, the cleavable linking group is cleavable by a peptidase or protease found in higher amount in pancreatic cancer cells. In one embodiment, the linker comprises the compound shown in FIG. 11.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

One problem addressed by the invention is related to spread of cancers (for example, pancreatic cancer) by metastasis and the development of cancer resistance to therapy. One of the drawbacks of currently used agents to slow down proliferation of cancer cells is that these agents turn the cells into cancer stem-like cells that are more likely develop resistance to targeted therapies, and likely to metastasize and spread the tumor. Currently, there are no solutions to prevent cancer metastasis. This invention provides compounds, compositions, methods and kits that inhibit cancer spread by metastasis and diminish the development stem-like properties.

Dual Inhibitor Compounds

In various embodiments, the present invention provides a compound that inhibits both HDAC and GSK3β. Compounds that inhibit both HDAC and GSK3β are also referred to as dual inhibitors herein.

In embodiments of the various aspects disclosed herein, the dual inhibitor compound is of Formula (IV):

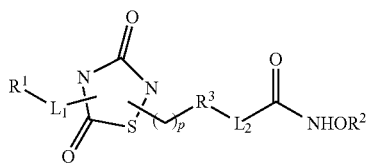

(IV)

wherein:
$L_1$ and $L_2$ are independently a linker;
$R^1$ is an aromatic moiety, alkyl, acyl, cyclyl or heterocyclyl, each of which can be optionally substituted;
$R^2$ is hydrogen, alkyl, cyclyl, heterocyclyl, aryl, or heteroaryl, each of which can be optionally substituted;
$R^3$ is absent or an aromatic moiety, which can be optionally substituted;
p is 0, 1, 2, 3, 4, 5, 6, 7, 8, 9, 10, 11, or 12; and
wherein one. $R^1$-$L_1$- is linked to one nitorgen of the thiadiazolidine ring and —$(CH_2)_p$—$R^3$-$L_2$-C(O)NHOR$^2$ is linked to the other nitorgen of the thiadiazolidine ring.

In some other embodiments of the various aspects disclosed herein, the compound is of Formula (V):

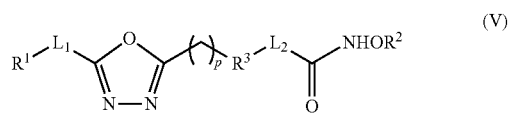

(V)

wherein:
$L_1$ and $L_2$ are independently a linker;
$R^1$ is an aromatic moiety, alkyl, acyl, cyclyl or heterocyclyl, each of which can be optionally substituted;
$R^2$ is hydrogen, lower alkyl, cyclyl, heterocyclyl, aryl, or heteroaryl, each of which can be optionally substituted;
$R^3$ is absent or an aromatic moiety, which can be optionally substituted; and
p is 0, 1, 2, 3, 4, 5, 6, 7, 8, 9, 10, 11 or 12.

In various compounds of Formula (IV) or (V), $R^1$ can be an optionally substituted aryl or lower alkyl. In some embodiments, $R^1$ in Formula (IV) or (V) can be selected independently from $C_1$-$C_{10}$alkyl, aryl or heteroaryl, each of which can be optionally substituted with 1, 2, 3 or 4 substituents.

In various embodiments, $R^1$ can be a lower alkyl group. In some embodiments, $R_1$ can be a $C_1$-$C_6$alkyl. Exemplary alkyl groups for $R^1$ include, but are not limited to methyl, ethyl, propyl, isopropyl, butyl, sec-butyl, isobutyl, tert-butyl, pentyl, neopentyl, and hexyl. In one embodiment, $R^1$ is methyl.

In various embodiments, $R^1$ is an optionally substituted aryl or optionally substituted heteroaryl selected from the group consisting of pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

In some embodiments, $R^1$ is an optionally substituted phenyl. Generally, the optionally substituted phenyl can be substituted with 1, 2, 3, 4 or 5 substituents selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. Preferably, the optionally substituted phenyl is substituted with one substituent. In one embodiment, the optionally substituted phenyl is 4-methoxyphenyl.

In various embodiments of Formula (IV) or (V), $R^2$ can be hydrogen, lower alkyl group, 3-8 membered cyclyl or heterocyclyl, or 5-8 membered aryl or heteroaryl, each of which can be optionally substituted. In some embodiments, $R^2$ is hydrogen or lower alkyl. In various embodiments $R^2$ can be $C_1$-$C_6$alkyl. Exemplary alkyl groups for $R^2$ include, but are not limited to methyl, ethyl, propyl, isopropyl, butyl, sec-butyl, isobutyl, tert-butyl, pentyl, neopentyl, and hexyl. In some embodiments, $R^2$ is H or methyl.

In various embodiments of Formula (IV) or (V), $R^3$ can be absent or an optionally substituted aryl or optionally substituted heteroaryl. Exemplary optionally substituted aryl and optionally substituted heteroaryl for $R_3$ include, but are not limited to pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, quinolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

In some embodiments, $R^3$ is an optionally substituted phenyl. the optionally substituted phenyl can be substituted with 1, 2, 3, or 4 substituents selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. Preferably, the optionally substituted phenyl is substituted with one substituent.

In some other embodiments, $R^3$ is absent.

In various embodiments of Formula (IV) or (V), p is 0, 1, 2, 3, or 5. Preferably, p is 0 or 1. In some embodiments, p is 0. In some other embodiments, p is 1.

In various embodiments, the linker is selected independently for each occurrence from the group consisting of a bond, $—(CH_2)_q—$, $—(CH_2)_qCH=CH(CH_2)_r—$, $—NH—$, $—NHC(O)(CH_2)_q—$, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12.

In various embodiments, $L_1$ is selected from a bond, $—(CH_2)_q—$, $(CH_2)_qCH=CH(CH_2)_r—$, $—NH—$, $—NHC(O)(CH_2)_q—$, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, $L_1$ is a bond or $—(CH_2)_q—$. Preferred values of q for $L_1$ include, but are not limited to 1, 2, 3, 4, 5 and 6. In some embodiments, $L_1$ is $—CH_2—$. In some other embodiments, $L_1$ is a bond. In still some other embodiments, $L_1$ is $—NH—$ In various embodiments, $L_2$ can be selected from a bond, $—(CH_2)_q—$, $—(CH_2)_qCH=CH(CH_2)_r—$, $—NH—$, $—NHC(O)(CH_2)_q—$, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, $L_2$ is a bond; $—NH—$; $—NHC(O)(CH_2)_q—$, wherein q is 4, 6, or 8; or $—CH_2CH=CH—$. In some embodiments, $L_2$ is a bond. In some other embodiments, $L_2$ is $—NH—$.

In the various compounds disclosed herein, $L_1$-$R_1$ is $—CH_2$-phenyl. In some other embodiments, $L_1$-$R_1$ is $CH_3$. In yet some other embodiments, $L_1$-$R_1$ is 4-methoxybenzyl.

In some embodiments, p is 0 or 1, and $R_3$ is phenyl. In some other embodiments, p is 0 and $R^3$ is absent.

In some compounds p is 0; $R^3$ is phenyl; and $L_2$ is a bond or $—NHC(O)(CH_2)_q—$, wherein q is 4, 6, or 8. In some other embodiments, p is 1; $R^3$ is phenyl; and $L_2$ is $—NHC(O)(CH_2)_q—$, wherein q is 6. In still some other embodiments, p is 0 and $L_2$ is $—CH_2CH=CH—$.

In some embodiments, a compound of Formula (IV) is a compound of Formula (VI):

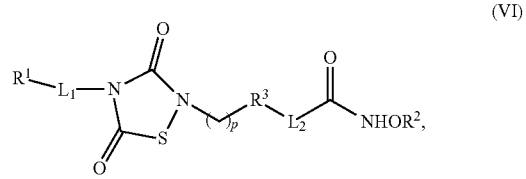

(VI)

wherein $R^1$, $R^2$, $R^3$, $L_1$, $L_2$ and p are as defined for Formula (IV).

In some embodiments, a compound of Formula (IV) is a compound of Formula (VII):

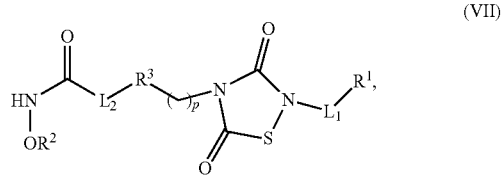

(VII)

wherein $R^1$, $R^2$, $R^3$, $L_1$, $L_2$ and p are as defined for Formula (IV).

In various embodiments, a compound according to Formula (IV) is a compound of Formula (I):

(I)

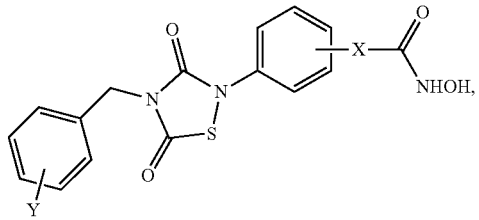

wherein X is a linker (e.g., L$_2$) and Y is absent or an substituent for an aromatic group. In some embodiments, Y is selected from the group consisting of alkyl, CF$_3$, NO$_2$, CO$_2$H, SO$_2$H, cyano, hydroxy, thiol, alkylthio, alkoxy, acyl, halogen, amino, alkyl amino, dialkylamino, and any combinations thereof. While only one Y substituent is shown, more than one Y, e.g. one, two, three, four or five Ys, can be present on the benzene ring. In some embodiments, Y is absent.

In various embodiments, X can be selected from a bond, —(CH$_2$)$_q$—, —(CH$_2$)$_q$CH=CH(CH$_2$)$_r$—, —NH—, —NHC(O)(CH$_2$)$_q$—, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, X is a bond; —NH—; —NHC(O)(CH$_2$)$_q$—, wherein q is 4, 6, or 8; or —CH$_2$CH=CH—. In some embodiments, X is —NH—.

In some embodiments, a compound of Formula (I) is a compound of Formula (I-1):

(I-1)

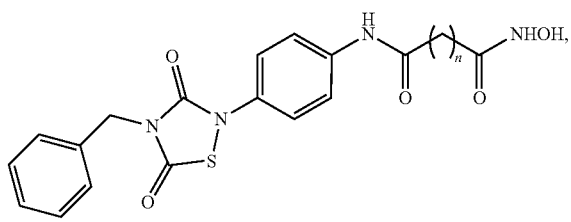

wherein n is 1, 2, 3, 4, 5, 6, 7, 8, 9, 10, 11, or 12.

In various embodiments of Formula (I-1), n is 4, 6, or 8, i.e., compounds of Formula (I-1a), (I-1b), or (I-1c):

(I-1a)

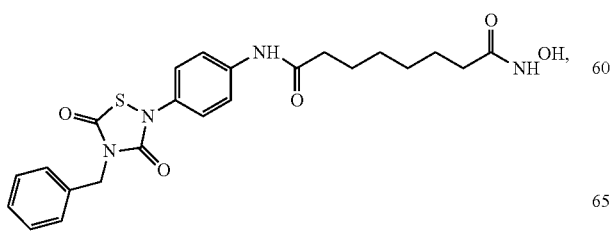

(I-1b)

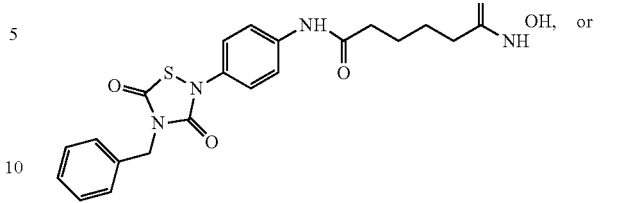

(I-1c)

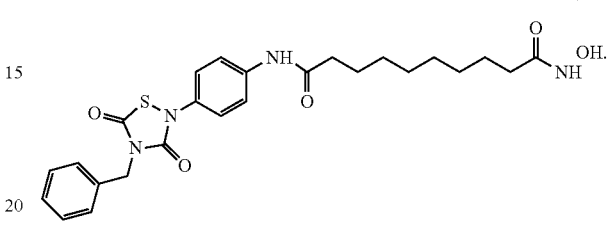

The compound of Formula (I-1a) is also referred to as ALB-185602 herein. The compound of Formula (I-1b) is also referred to as ALB-185644 herein. The compound of Formula (I-1c) is also referred to as ALB-185643 herein.

In some embodiments, a compound of Formula (I) is a compound of Formula (I-2):

(I-2)

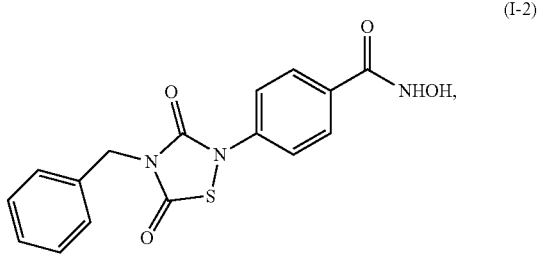

In some embodiments, a compound of Formula (I) is a compound of Formula (I-3):

(I-3)

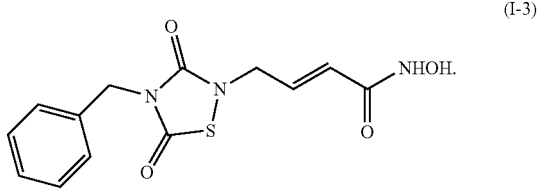

In various embodiments of Formula (IV) is a compound of Formula (II):

(II)

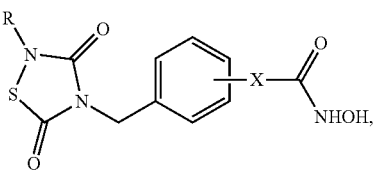

wherein X is a linker group, and R is -L$_1$R$^1$.

In various embodiments, X can be selected from a bond, —(CH$_2$)$_q$—, —(CH$_2$)$_q$CH=CH(CH$_2$)$_r$—, —NH—, —NHC(O)(CH$_2$)$_q$—, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, X is a bond; —NH—; —NHC(O)(CH$_2$)$_q$—, wherein q is 4, 6, or 8; or —CH$_2$CH=CH—. In some embodiments, X is —NH—.

In various embodiments, -L$_1$R$^1$ can be selected from a bond —R$^1$, —(CH$_2$)$_q$—R$^1$, —(CH$_2$)$_q$CH=CH(CH$_2$)$_r$—R$^1$, —NH—R$^1$, —NHC(O)(CH$_2$)$_q$—R$^1$, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, -L$_1$R$^1$ is a bond-R$^1$; —NH—R$^1$; —NHC(O)(CH$_2$)$_q$—R$^1$, wherein q is 4, 6, or 8; or —CH$_2$CH=CH—R$^1$.

In some embodiments of compounds of Formula (II), -L$_1$R$^1$ is an optionally substituted alkyl. In one embodiment, R is methyl.

Exemplary compounds of Formula (II) include, but are not limited to, a compound of Formula (II-1):

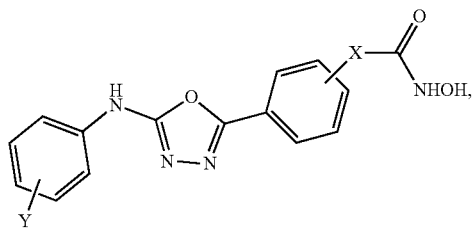

In various embodiments, a compound of Formula (V) is a compound of Formula (ITT):

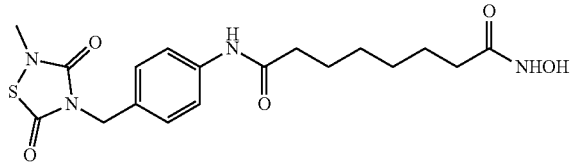

wherein X is a linker (e.g., L$_2$) and Y is absent or an substituent for an aromatic group. In some embodiments, Y is selected from the group consisting of alkyl, CF$_3$, NO$_2$, CO$_2$H, SO$_2$H, cyano, hydroxy, thiol, alkylthio, alkoxy, acyl, halogen, amino, alkyl amino, dialkylamino, and any combinations thereof. While only one Y substituent is shown, more than one Y, e.g. one, two, three, four or five Ys, can be present on the benzene ring.

In various embodiments, at least one Y is present and is an alkoxy group. Exemplary alkoxy groups for Y include, but are not limited to, methoxy, ethoxy, propyloxy, tert-butoxy, n-propyloxy, iso-propyloxy, n-butyloxy, iso-butyloxy, and the like. In one embodiment, Y is methoxy.

In various embodiments, X can be selected from a bond, —(CH$_2$)$_q$—, —(CH$_2$)$_q$CH=CH(CH$_2$)$_r$—, —NH—, —NHC(O)(CH$_2$)$_q$—, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, X is a bond; —NH—; —NHC(O)(CH$_2$)$_q$—, wherein q is 4, 6, or 8; or —CH$_2$CH=CH—. In some embodiments, X is a bond.

In some embodiments, a compound of Formula (III) is a compound of Formula (III-1):

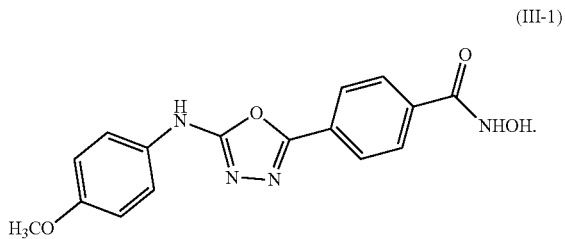

The compound of Formula (III-1) is also referred to as ALB-185357 herein. In various embodiments, a compound of Formula (V) is a compound of Formula (IIIb):

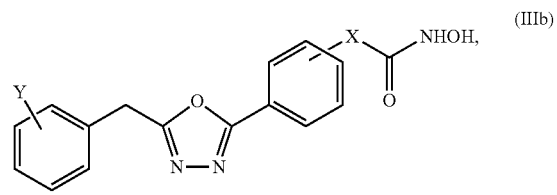

wherein X is a linker (e.g., L$_2$) and Y is absent or an substituent for an aromatic group. In some embodiments, Y is selected from the group consisting of alkyl, CF$_3$, NO$_2$, CO$_2$H, SO$_2$H, cyano, hydroxy, thiol, alkylthio, alkoxy, acyl, halogen, amino, alkyl amino, dialkylamino, and any combinations thereof. While only one Y substituent is shown, more than one Y, e.g. one, two, three, four or five Ys, can be present on the benzene ring.

In various embodiments, at least one Y is present and is an alkoxy group. Exemplary alkoxy groups for Y include, but are not limited to, methoxy, ethoxy, propyloxy, tert-butoxy, n-propyloxy, iso-propyloxy, n-butyloxy, iso-butyloxy, and the like. In one embodiment, Y is methoxy.

In various embodiments, X can be selected from a bond, —(CH$_2$)$_q$—, —(CH$_2$)$_q$CH=CH(CH$_2$)$_r$—, —NH—, —NHC(O)(CH$_2$)$_q$—, and any combinations thereof, wherein q is independently for each occurrence 1, 2, 3, 4, 5, 6, 7, 8, 9, 10, 11 or 12 and wherein r is independently for each occurrence 0, 1, 2, 3, 4, 5, 6, 7, 8, 9, 10, 11 or 12. In some embodiments, X is a bond; —NH—; —NHC(O)(CH$_2$)$_q$—, wherein q is 4, 6, or 8; or —CH$_2$CH=CH—. In one embodiment X is a bond.

In some embodiments, a compound of Formula (IIIb) is a compound of Formula (IIIb-1) having the structure:

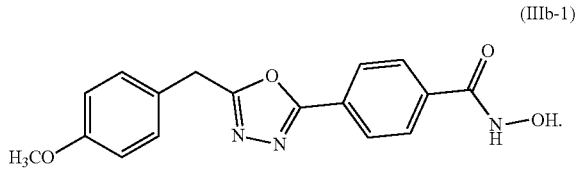 [SMILES: COc1ccc(Cc2nnc(-c3ccc(C(=O)NO)cc3)o2)cc1]

The compound of Formula (IIIb-1) is also referred to as ALB-188540 herein.

Compounds disclosed herein can be prepared beginning with commercially available starting materials and utilizing general synthetic techniques and procedures known to those skilled in the art. Chemicals can be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

Figure 8:
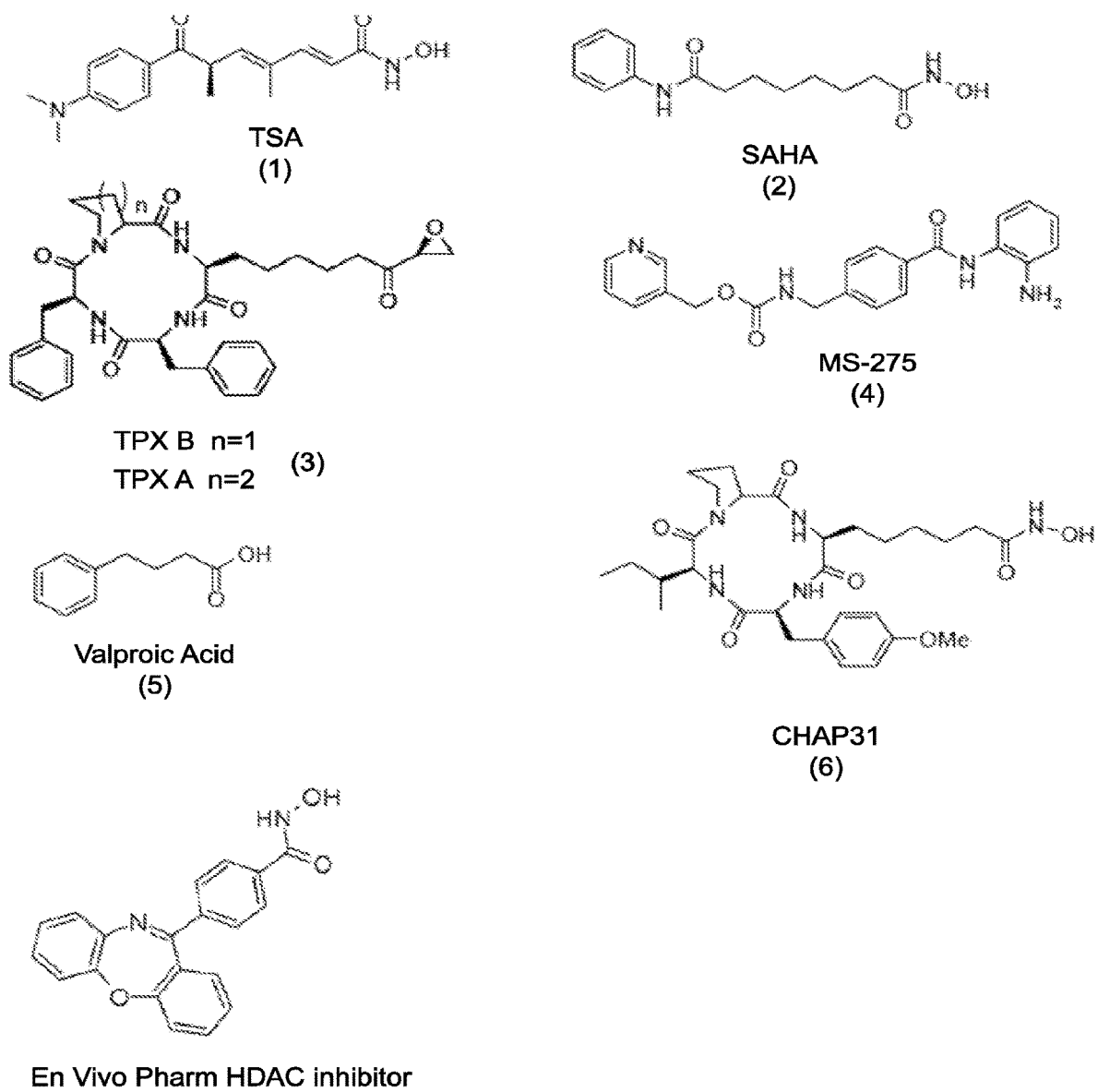
FIG. 8 depicts, in accordance with various embodiments of the invention, the structures of examples of HDAC inhibitors. For example, subcroylanilide hydroxamic acid (SAHA) binds to the active site of HDAC and act as a chelator for Zinc ions also found in the active site of HDAC. More information may be found in Ekou et al. (Histone Deacetylase Inhibitors: Synthesis of Tetrapeptide Analogue SAHA/TPX; J. Chem. 2011; 8(S1): S79-S84), which is incorporated herein by reference in its entirety as though fully set forth.
Figure 9:
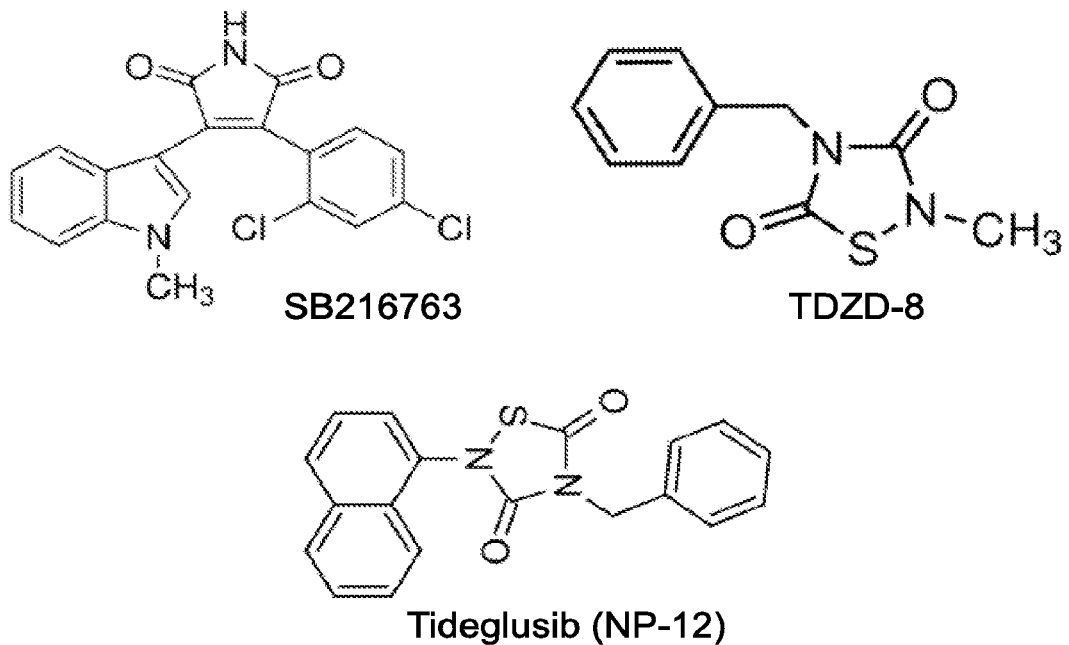
FIG. 9 depicts, in accordance with various embodiments of the invention, the structures of examples of GSK3β inhibitors. For example, SB216763 is an ATP analog; TDZD-8, a thiadiazolidinone derivative, is a potent and selective small molecule non ATP-competitive GSK3β inhibitor; and Tideglusib (NP-12; 4-Benzyl-2-(naphthalen-1-yl)-1,2,4-thiadiazolidine-3,5-dione) is a potent and selective small molecule non ATP-competitive GSK3β inhibitor.

Synthesis of various exemplary compounds of Formula (IV) is shown below in Schemes I, II, III and IV, and synthesis of some exemplary compounds of Formula (V) is shown below in Scheme V. It is noted that an ordinarily skilled arisan can easily adapt these for preparing anyone of the compounds of Formula (I)-(VI). Scheme I depicts, in accordance with various embodiments of the invention, reaction schemes toward compounds of Formula I, for examples, targets 1a, 1b and 1c (Formula I-1a, 1b and 1c). Scheme II depicts, in accordance with various embodiments of the invention, reaction schemes toward compounds of Formula I, for examples, target 2 (Formula I-2). Target 2 is similar to En Vivo Pharma HDAC inhibitor shown in FIG. 8. Scheme III depicts, in accordance with various embodiments of the invention, reaction schemes toward compounds of Formula I, for examples, target 3 (Formula I-3). Target 3 has a smaller zinc-binding moiety. Scheme IV depicts, in accordance with various embodiments of the invention, reaction schemes toward compounds of Formula II, for examples, target 4 (Formula II-1). Target 4 combines the benzamide moiety of SAHA and benzyl moiety of TDZD-8. Scheme V depicts, in accordance with various embodiments of the invention, reaction schemes toward compounds of Formula III, for examples, target 5 (Formula III-1). Target 5 is an analog of GSK3β inhibitors reported in Khanfar et a. (Discovery of novel GSK-3β inhibitors with potent in vitro and in vivo activities and excellent brain permeability using combined ligand- and structure-based virtual screening; J Med Chem. 2010 Dec. 23; 53(24):8534-45), which is incorporated herein by reference in its entirety as though fully set forth. The hydroxamic acid moiety of target 5 can engage in the critical H-bonds required for GSK3β activity as well as serving as the zinc-binding moiety for HDAC inhibition.

Targets 1a, 1b and 1c

Scheme I

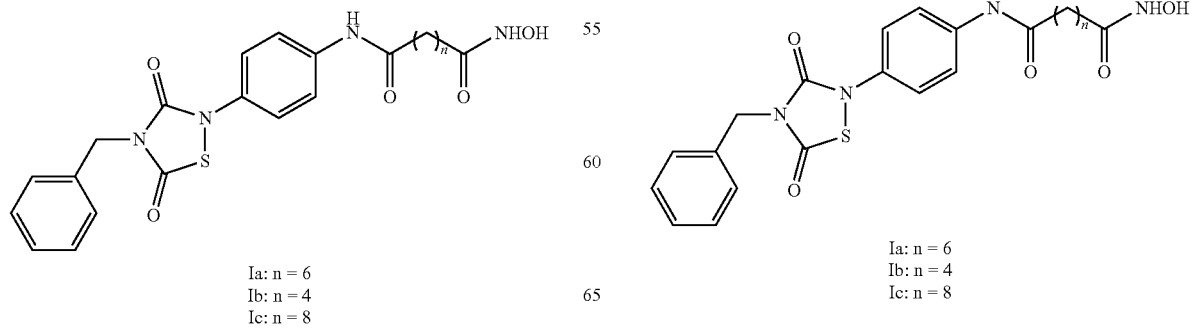

37
Target 2
38
Tart 3
Scheme II
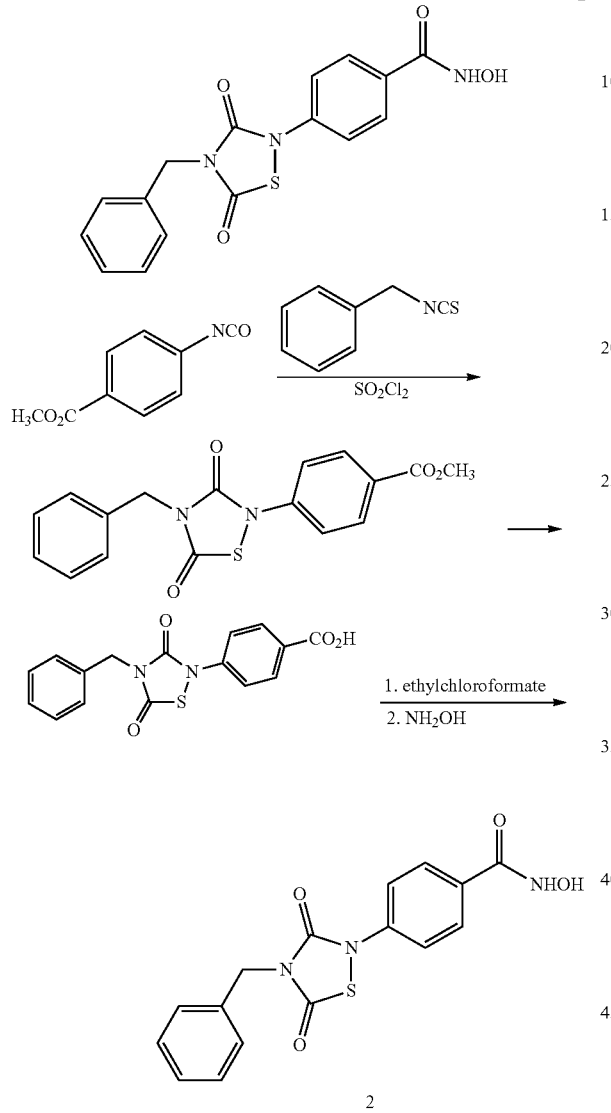
Scheme III
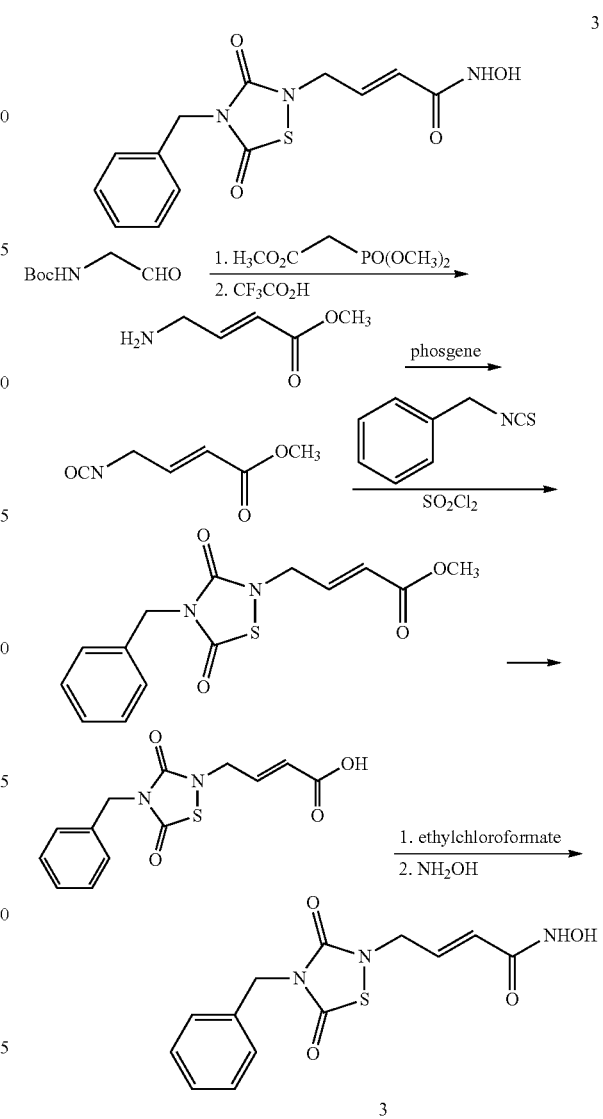
Target 4
Scheme IV
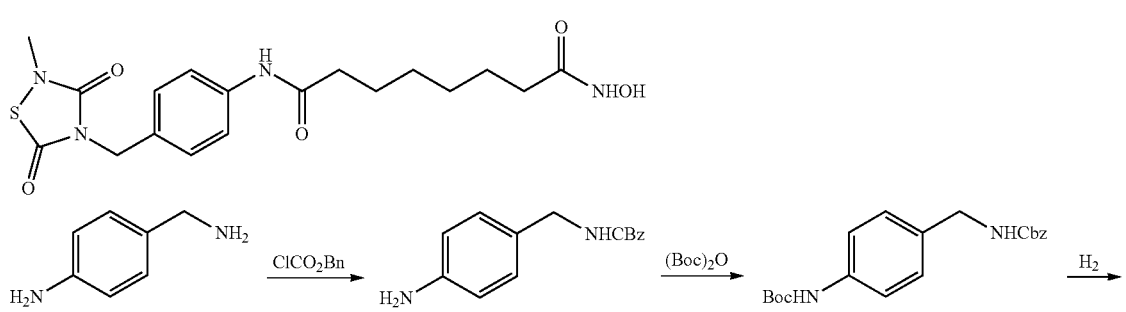

39

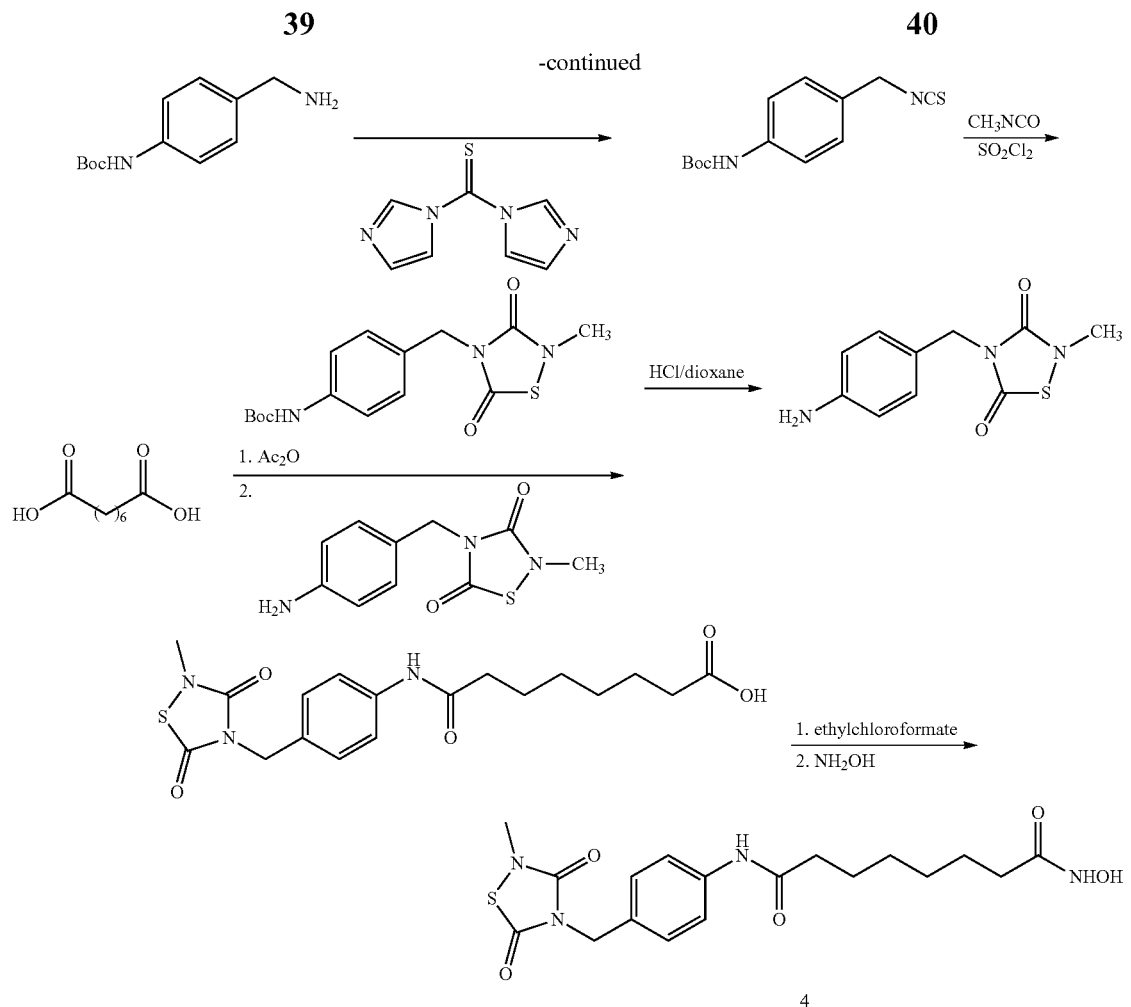

40

-continued

Target 5

Scheme V

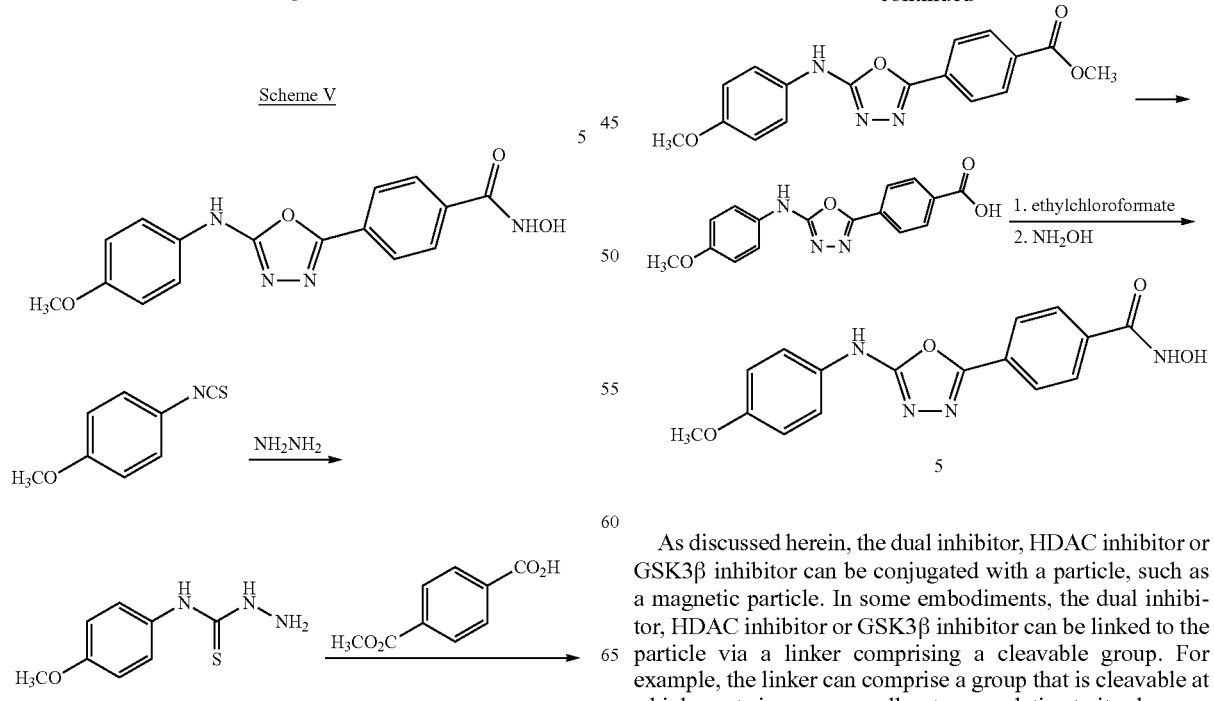

As discussed herein, the dual inhibitor, HDAC inhibitor or GSK3β inhibitor can be conjugated with a particle, such as a magnetic particle. In some embodiments, the dual inhibitor, HDAC inhibitor or GSK3β inhibitor can be linked to the particle via a linker comprising a cleavable group. For example, the linker can comprise a group that is cleavable at a higher rate in a cancer cell or tumor relative to its cleavage in a non-cancer cell. In some embodiments, the linker can comprise a group that is cleavable by an enzyme present at a higher amount in a cancer cell or tumor relative to its amount in a non-cancer cell. In some embodiments, the linker can comprise a cleavable group that is cleaved by a peptidase present at a higher amount in a cancer cell or tumor relative to its amount in a non-cancer cell. In some embodiments, the linker comprises a cleavable group that is cleaved by Cathepsin G.

Figure 10:
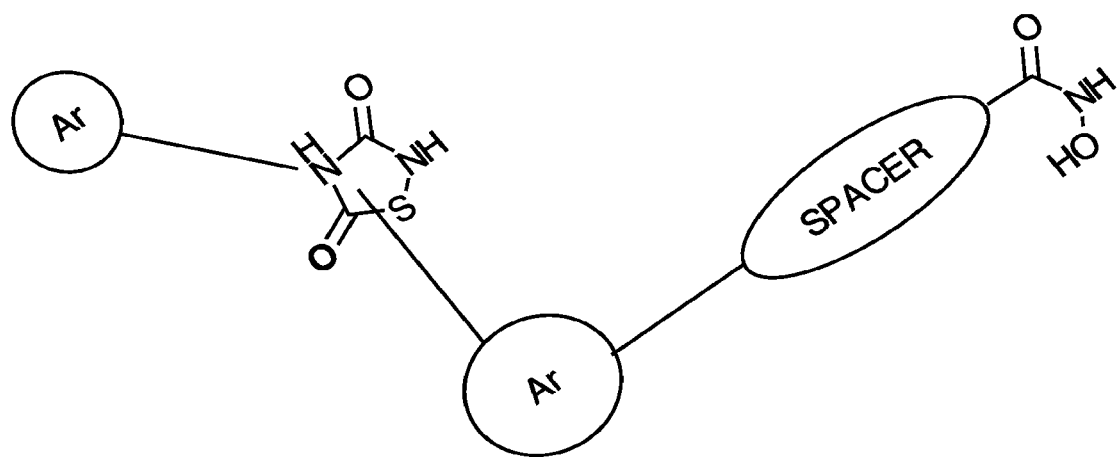
FIG. 10 depicts, in accordance with various embodiments of the invention, one non-limiting example of the inventors' compounds that inhibit both HDAC and GSK3β. Ar refers to aromatic moiety and spacer refers to carbon linkers.

FIGS. 10-12 show components of an exemplar system having a dual inhibitor (FIG. 10), or one each of a HDAC inhibitor and a GSK3β inhibitor, and prodrug moieties such as cleavable enzyme substrates and nanoparticles. For example, the dual inhibitor, or one each of a HDAC inhibitor and a GSK3β inhibitor, is attached to a peptidase substrate (FIG. 11) which, in turn, can be be attached to a magnetic particle (FIG. 12). Attachment to a magnetic vehicle allows for the guidance of the agents to the tumor. Because tumors have high concentrations of Cathepsin G, the inhibitors are released at the tumor.

As a non-limiting example, an inhibitor (e.g., a dual inhibitor, or one each of a HDAC inhibitor and a GSK3β inhibitor) can be attached to a cleavable enzyme substrate (e.g., a Cathepsin G substrate Suc-AAPF-pNA from Santa Cruz Biotechnology) using protocols recommended by the manufacturer and/or known by one of ordinary skill in the art. As a non-limiting example, a cleavable enzyme substrate (e.g., a Cathepsin G substrate Sue-AAPF-pNA from Santa Cruz Biotechnology) can be attached to a magnetic particle (e.g., siMAG from Chemicell) using protocols recommended by the manufacturer and/or known by one of ordinary skill in the art (e.g., free carboxyl conjugation, carboiimide method, and Mannich reaction.

Generally, the particle can be of any shape or form, e.g., spherical, rod, elliptical, cylindrical, capsule, or disc; and these particles can be part of a network or an aggregate. Without limitations, the particle can have any size from nm to millimeters. In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm. Generally, the particles disclosed herein are nanoparticles and have an average diameter of from about 5 nm to about 500 nm. In some embodiments, the particles have an average diameter of from about 75 nm to about 500 nm, from about 25 nm to about 250 nm, from about 50 nm to about 150 nm, from about 75 nm to about 125 nm, from about 50 nm to about 500 nm, from about 75 nm to about 200 nm, from about 100 to about 175 nm, from about 125 nm to about 175 nm, from about 40 nm to about 90 nm, or from about 50 nm to about 80 nm.

In some embodiments a nanoparticle can be less than about 1 um in diameter, e.g., about 1 um or less in diameter, about 500 nm or less in diameter, about 400 nm or less in diameter, about 300 nm or less in diameter, about 200 nm or less in diameter, about 100 nm or less in diameter, about 50 nm or less in diameter, or about 10 nm or less in diameter. In some embodiments a nanoparticle can be less than 1 um in diameter, e.g., 1 um or less in diameter, 500 nm or less in diameter, 400 nm or less in diameter, 300 nm or less in diameter, 200 nm or less in diameter, 100 nm or less in diameter, 50 nm or less in diameter, or 10 nm or less in diameter. In some embodiments, the nanoparticles in a composition can be from about 1 nm to about 1 um in diameter, e.g. from about 1 nm to about 500 nm in diameter, from about 1 nm to about 200 nm in diameter, from about 10 nm to about 200 nm in diameter, from about 100 nm to about 200 nm in diameter, or from about 10 nm to about 100 nm in diameter. In some embodiments, the nanoparticles in a composition can be from 1 nm to 1 um in diameter, e.g. from 1 nm to 500 nm in diameter, from 1 nm to 200 nm in diameter, from 10 nm to 200 nm in diameter, from 100 nm to 200 nm in diameter, or from 10 nm to 100 nm in diameter.

In some embodiments, nanoparticles can be selected to be of specific sizes, e.g. less than about 200 nm in diameter. Methods of selecting nanoparticles of a particular size and/or range of sizes are known in the art and can include, by way of non-limiting example, filtration, sedimentation, centrifugation, and/or chromatographic methods, e.g. SEC.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axis of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The particles can be, e.g., monodispersed or polydispersed and the variation in diameter of the particles of a given dispersion can vary. In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In various embodiments, the particle can comprise a magnetic material. As used herein, the term "magnetic material" refers to a material or substance that is influenced by a magnetic field, i.e. relative permeability ($\mu_r$) of the material is greater than unity. Such magnetic materials are intended to include those which are referred to as ferromagnetic, diamagnetic, paramagnetic, and superparamagnetic. As is the conventional understanding given that term, superparamagnetic materials exhibit magnetic properties only when in an externally applied magnetic field, and otherwise exhibit essentially no magnetic properties; and their total magnetism is greater than the sum of that of the individual particles considered separately. If the particle size of the magnetic material is sufficiently small, the magnetic material will most likely be superparamagnetic. The magnetic properties of the particle comprising the magnetic material are greatly influenced by the saturation magnetization, size, and concentration of magnetic material, as well as the strength of the external magnetic field.

The magnetic material can be any molecule, composition, particle, or substance that exhibits magnetic properties when incorporated into the matrix. The magnetic materials can be selected from the group of elements having atomic numbers 21-29, 42, 44, and 57-70, elements having atomic numbers 24-29 or 62-69 being especially preferred. Preferably, a magnetic material is selected from the group including but not limited to, rare earth metals (such as gadolinium, terbium, dysprosium, holmium, erbium and europium), transient metals (such as iron, nickel, cobalt, magnesium chromium and copper), noble metals (such as rhodium, palladium), their oxides, compositions, combinations, solid dispersions, and alloys.

In some embodiments, the magnetic material is selected from the group consisting of maghemite ($Fe_2O_3$), magnetite ($Fe_3O_4$), strontium ferrite, samarium-cobalt, neodymium-iron-boron (NIB), lodestone, pyrrhotite, $BaFe_{12}O_{19}$, Alnico magnet alloy, transfer salts of decamethylmetallocenes with 7,7,8,8-tetracyano-p-quinodimethane (TCNQ) or tetracyanoethenide (TCNE) (such as $[Fe(Cp^*)_2]^+[TCNE]^-$, $[Fe(Cp^*)_2]^+[TCNQ]^-$, $[Cr(Cp^*)_2]^+[TCNE]^-$, $[Cr(Cp^*)_2]^+[TCNQ]^-$, $[Mn(Cp^*)_2]^+[TCNE]^-$, and $[Mn(Cp^*)_2]^+[TCNQ]^-$), hexylammonium trichlorocuprate(II) ($CuCl_3(C_6H_{11}NH_3)$, Fe based amorphous magnetic powders, and combinations thereof.

In some embodiments, the magnetic material comprising particle is a magnetic nanoparticle. Magnetic nanoparticles are a class of nanoparticle which can be manipulated using magnetic field. Such particles commonly consist of magnetic elements such as iron, nickel and cobalt and their chemical compounds. Magnetic nanoparticles are well known and methods for their synthesis are described in the art, for example, in U.S. Pat. Nos. 6,878,445; 5,543,158; 5,578,325; 6,676,729; 6,045,925 and 7,462,446, and U.S. Pat. Pub. No. 2005/0025971; No. 2005/0200438; No. 2005/0201941; No. 2005/0271745; No. 2006/0228551; No. 2006/0233712; No. 2007/01666232 and No. 2007/0264199, contents of all of which are incorporated herein by reference in their entirety.

In some embodiments, the particle is siMAG magnetic beads, available from, for example, chemicell GmbH (Berlin, Germany). Both amine functionalized and carboxyl functionalized SiMAG beads are available. Thus, any method of coupling taking advantage of the amine or the carboxyl group can be used for conjugating the dual inhibitor, HDAC inhibitor or GSK3β inhibitor to the siMAG beads. For example, cabodiimide based coupling reactions can be used for both the amine functionalized and carboxyl functionalized siMAG beads. Mannich reaction can be used for the amine funtionalized siMAG beads.

Treatment Methods

In various embodiments, the present invention provides a method of treating, preventing, reducing the likelihood of having, reducing the severity of and/or slowing the progression of a condition in a subject. The method consists of or consists essentially of or comprises: administering a therapeutically effective amount of a dual inhibitor to the subject, thereby treating, preventing, reducing the likelihood of having, reducing the severity of and/or slowing the progression of the condition in the subject.

In various embodiments, the method further comprises administration or treatment with one or more additional cancer therapies. Examples of anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the dual inhibitor.

In those embodiments where a combination therapy regimen is applied, the dual inhibitor and one or more anti-cancer therapeutic agents as described herein are administered in a therapeutically effective or synergistic amount. As used in such embodiments encompassing combination therapies, a therapeutically effective amount is such that co-administration of the dual inhibitor and one or more other anti-cancer therapeutic agent results in reduction or inhibition of the cancer as described herein. A "therapeutically synergistic amount" is that amount of dual inhibitor and one or more other anti-cancer therapeutic agent necessary to synergistically or significantly reduce or eliminate conditions or symptoms associated with a particular cancer.

In some embodiments, the dual inhibitor and one or more other anti-cancer therapeutic agent can be administered simultaneously or sequentially in an amount and for a time sufficient to reduce or eliminate the occurrence or recurrence of a tumor, a dormant tumor, or a micrometastases. In some embodiments, the dual inhibitor and one or more other therapeutic agents can be administered as maintenance therapy to prevent or reduce the likelihood of recurrence of the tumor.

Without limitation, the dual inhibitor and the one or more other anti-cancer therapeutic agent can be provided in separate compositions or in the same composition. Further, the dual inhibitor and the one or more other anti-cancer therapeutic agent can be administered concurrently or sequentially. In certain embodiments, the dual inhibitor is administered before, during or after administering the one or more other anti-cancer therapeutic agent.

In various embodiments, the method further comprises: administering a chemotherapeutic agent to the subject. In some embodiments, the dual inhibitor and the chemotherapeutic agent are provided in one composition. In other embodiments, the dual inhibitor and the chemotherapeutic agent are provided in separate compositions. In various embodiments, the dual inhibitor and the chemotherapeutic agent are administered concurrently or sequentially. In certain embodiments, the dual inhibitor is administered before, during or after administering the chemotherapeutic agent.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy.

In still further embodiments, the dual inhibitor is attached to a cleavable enzyme substrate and the cleavable enzyme substrate is attached to a magnetic particle. In one embodiment, the cleavable enzyme substrate is a substrate of an enzyme enriched in a cancer or tumor. In another embodiment, the cleavable enzyme substrate is a substrate of a peptidase enriched in a cancer or tumor. In certain embodiment, the cleavable enzyme substrate is a substrate of Cathepsin G. In various embodiments, the method further comprises using a magnetic field to guide the dual inhibitor to a cancer or tumor.

In some embodiments, the dual inhibitor is a compound of Formula IV, Formula V, Formula VI, or Formula VII. In various embodiments, the dual inhibitor is a compound of Formula I, Formula II, Formula III, IIIb, Formula I-1, Formula I-1a, Formula I-1 b, Formula I-1c, Formula I-2, Formula I-3, Formula II-I, Formula III-I, Formula-IIIb-1, or a combination thereof.

In accordance with the invention, the dual inhibitor can be administered using the appropriate modes of administration, for instance, the modes of administration recommended by the manufacturer. In accordance with the invention, various routes can be utilized to administer the dual inhibitor of the claimed methods, including but not limited to aerosol, nasal, oral, transmucosal, transdermal, parenteral, implantable pump, continuous infusion, topical application, capsules and/or injections. In various embodiments, the dual inhibitor is administered topically, intravascularly, intravenously, intraarterially, intratumorally, intramuscularly, subcutaneously, intraperitoneally, intranasally, or orally.

Typical dosages of an effective amount of the dual inhibitor can be in the ranges recommended by the manufacturer where known therapeutic compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the dual inhibitor may be administered once a day (SID/QD), twice a day (BID), three times a day (TID), four times a day (QID), or more, so as to administer an effective amount of the dual inhibitor to the subject, where the effective amount is any one or more of the doses described herein.

In some embodiments, the dual inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the dual inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg, or a combination thereof. In various embodiments, the dual inhibitor is administered about 1-3 times per day, 1-7 times per week, or 1-9 times per month. In various embodiments, the dual inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the dual inhibitor is administered once, twice, three or more times.

In various embodiments, the effective amount of the dual inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µM, or a combination thereof.

In various embodiments, the effective amount of the dual inhibitor is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day, or a combination thereof. Here, "µg/kg/day" or "mg/kg/day" refers to µg or mg per kg body weight of the subject per day.

In various embodiments, the present invention provides a method of treating, preventing, reducing the likelihood of having, reducing the severity of and/or slowing the progression of a condition in a subject. The method consists of or consists essentially of or comprises: administering a therapeutically effective amount of a HDAC inhibitor and a GSK3β inhibitor to the subject, thereby treating, preventing, reducing the likelihood of having, reducing the severity of and/or slowing the progression of the condition in the subject.

In some embodiments, the HDAC inhibitor and the GSK3β inhibitor are provided in one composition. In other embodiments, the HDAC inhibitor and the GSK3β inhibitor are provided in separate compositions. In various embodiments, the HDAC inhibitor and the GSK3β inhibitor are administered concurrently or sequentially. In certain embodiments, the HDAC inhibitor is administered before, during or after administering the GSK3β inhibitor.

In various embodiments, the method further comprises administration or treatment with one or more additional cancer therapies in addition to the administering the HDAC inhibitor and the GSK3β inhibitor. In those embodiments where a combination therapy regimen is applied, the HDAC inhibitor, the GSK3β inhibitor and one or more anti-cancer therapeutic agents as described herein are administered in a therapeutically effective or synergistic amount. As used in such embodiments encompassing combination therapies, a therapeutically effective amount is such that co-administration of the the HDAC inhibitor and the GSK3β inhibitor and one or more other anti-cancer therapeutic agent results in reduction or inhibition of the cancer as described herein. In this context, a "therapeutically synergistic amount" is that amount of the HDAC inhibitor and the GSK3β inhibitor and one or more other anti-cancer therapeutic agent necessary to synergistically or significantly reduce or eliminate conditions or symptoms associated with a particular cancer.

In some embodiments, the HDAC inhibitor, the GSK3β inhibitor and one or more other anti-cancer therapeutic agent can be administered simultaneously or sequentially in an amount and for a time sufficient to reduce or eliminate the occurrence or recurrence of a tumor, a dormant tumor, or a micrometastases. In some embodiments, the the HDAC inhibitor, the GSK3β inhibitor and one or more other therapeutic agents can be administered as maintenance therapy to prevent or reduce the likelihood of recurrence of the tumor.

Without limitation, at least one of the HDAC inhibitor or the GSK3β inhibitor and the one or more other anti-cancer therapeutic agent can be provided in separate compositions or in the same composition. Further, the dual inhibitor and the one or more other anti-cancer therapeutic agent can be administered concurrently or sequentially. In certain embodiments, the dual inhibitor is administered before, during or after administering the one or more other anti-cancer therapeutic agent.

In some embodiments, at least one of the HDAC inhibitor and/or the GSK3β is provided in the same composition as the additional anti-cancer therapeutic agent. In some embodiments, the HDAC inhibitor, the GSK3β inhibitor and the additional anti-cancer therapeutic agent are provided in one composition. In other embodiments, the HDAC inhibitor, the GSK3β inhibitor and the additional anti-cancer therapeutic agent are provided in separate compositions. In various embodiments, the HDAC inhibitor, the GSK3β and the additional anti-cancer therapeutic agent are administered concurrently or sequentially. In certain embodiments, at least one of the HDAC inhibitor or the GSK3β inhibitor is administered before, during or after administering the additional anti-cancer therapeutic agent.

In various embodiments, the method further comprises: administering a chemotherapeutic agent to the subject in addition to the HDAC inhibitor and the GSK3β inhibitor. In some embodiments, at least one of the HDAC inhibitor and/or the GSK3β is provided in the same composition as the additional chemotherapeutic agent. In some embodiments, the HDAC inhibitor, the GSK3β inhibitor and the additional chemotherapeutic agent are provided in one composition. In other embodiments, the HDAC inhibitor, the GSK3β inhibitor and the chemotherapeutic agent are provided in separate compositions. In various embodiments, the HDAC inhibitor, the GSK3β and the chemotherapeutic agent are administered concurrently or sequentially. In certain embodiments, at least one of the HDAC inhibitor or the GSK3β inhibitor is administered before, during or after administering the chemotherapeutic agent.

In addition administering the HDAC inhibitor and the GSK3β inhibitor, the subject can be subjected to radiation therapy.

In still further embodiments, the HDAC inhibitor and/or the GSK3β inhibitor are attached to a cleavable enzyme substrate and the cleavable enzyme substrate is attached to a magnetic particle. In one embodiment, the cleavable enzyme substrate is a substrate of an enzyme enriched in a cancer or tumor. In another embodiment, the cleavable enzyme substrate is a substrate of a peptidase enriched in a cancer or tumor. In certain embodiment, the cleavable enzyme substrate is a substrate of Cathepsin G. In various embodiments, the method further comprises using a magnetic field to guide the HDAC inhibitor and/or the GSK3β inhibitor to a cancer or tumor.

In various embodiments, the HDAC inhibitor is SAHA, TSA, TPX, MS-275, Valproic Acid, or CHAP31, or a functional equivalent, analog, derivative or salt thereof, or a combination thereof. In various embodiments, the GSK3β inhibitor is SB216763, TDZD-8, or Tideglusib (NP-12), or a functional equivalent, analog, derivative or salt thereof, or a combination thereof.

In accordance with the invention, the HDAC inhibitor and the GSK3β inhibitor can be administered using the appropriate modes of administration, for instance, the modes of administration recommended by the manufacturer for each of the HDAC inhibitor and the GSK3β inhibitor. In accordance with the invention, various routes can be utilized to administer the HDAC inhibitor and the GSK3β inhibitor of the claimed methods, including but not limited to aerosol, nasal, oral, transmucosal, transdermal, parenteral, implantable pump, continuous infusion, topical application, capsules and/or injections. In various embodiments, the HDAC inhibitor is administered topically, intravascularly, intravenously, intraarterially, intratumorally, intramuscularly, subcutaneously, intraperitoneally, intranasally, or orally. In various embodiments, the GSK3β inhibitor is administered topically, intravascularly, intravenously, intraarterially, intratumorally, intramuscularly, subcutaneously, intraperitoneally, intranasally, or orally.

Typical dosages of an effective amount of the HDAC inhibitor and/or the GSK3β inhibitor can be in the ranges recommended by the manufacturer where known therapeutic compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the HDAC inhibitor and/or the GSK3β inhibitor can be administered once a day (SID/QD), twice a day (BID), three times a day (TID), four times a day (QID), or more, so as to administer an effective amount of the HDAC inhibitor and/or the GSK3β inhibitor to the subject, where the effective amount is any one or more of the doses described herein.

In various embodiments, the HDAC inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the HDAC inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg, or a combination thereof. In various embodiments, the HDAC inhibitor is administered about 1-3 times per day, 1-7 times per week, or 1-9 times per month. In various embodiments, the HDAC inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the HDAC inhibitor is administered once, twice, three or more times. In one embodiment, the HDAC inhibitor is SAHA, or a functional equivalent, analog, derivative or salt of SAHA.

In some embodiments, the GSK3β inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the GSK3β inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg, or a combination thereof. In various embodiments, the GSK3β inhibitor is administered about 1-3 times per day, 1-7 times per week, or 1-9 times per month. In various embodiments, the GSK3β inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the GSK3β inhibitor is administered once, twice, three or more times. In one embodiment, the GSK3β inhibitor is TDZD-8, or a functional equivalent, analog, derivative or salt of TDZD-8. In another embodiment, the GSK3β inhibitor is Tideglusib, or a functional equivalent, analog, derivative or salt of Tideglusib.

In various embodiments, the effective amount of the HDAC inhibitor and/or GSK3β inhibitor are any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µM, or a combination thereof.

In various embodiments, the effective amount of the HDAC inhibitor and/or GSK3β inhibitor are any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day, or a combination thereof. Here, "µg/kg/day" or "mg/kg/day" refers to µg or mg per kg body weight of the subject per day.

In various embodiments, the subject is a human. In some embodiments, the subject is a mammalian subject including but not limited to human, monkey, ape, dog, cat, cow, horse, goat, pig, rabbit, mouse and rat.

In various embodiments, the condition is cancer or tumor. In some embodiments, the condition is pancreatic cancer. In some embodiments, the dual inhibitor, the HDAC inhibitor and/or GSK3β inhibitor can be administered at the prevention stage of a condition (i.e., when the subject has not developed the condition but is likely to or in the process to develop the condition). In other embodiments, the dual inhibitor, the HDAC inhibitor and/or GSK3β inhibitor can be administered at the treatment stage of a condition (i.e., when the subject has already developed the condition). As a non-limiting example, the target condition is pancreatic cancer. In this exemplar situation, the patient may be treated with the methods described herein when the patient has not yet developed pancreatic cancer, or is likely to develop pancreatic cancer, or is in the process of developing pancreatic cancer, or has already developed pancreatic cancer.

Pharmaceutical Compositions

In various embodiments, the present invention provides a composition that consists of or consists essentially of or comprises a dual inhibitor of HDAC and GSK3β. In accordance with the present invention, the composition can be used for treating, preventing, reducing the likelihood of having, reducing the severity of and/or slowing the progression of a condition in a subject.

In various embodiments, the dual inhibitor is a compound of Formula I, Formula II, Formula III, Formula I-1, Formula I-1a, Formula I-1b, Formula I-1c, Formula I-2, Formula I-3, Formula II-1, Formula III-1, Formula IIIb, Formula IIIb-1, Formula IV, Formula V, Formula VI, Formula VII, or a combination thereof. In some embodiments, the dual inhibitor in the composition is provided in mg dual inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the dual inhibitor in the composition is provided in µg dual inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg, or a combination thereof.

In various further embodiments, the composition further comprises a cleavable enzyme substrate and a magnetic particle, wherein the dual inhibitor is attached to the cleavable enzyme substrate and the cleavable enzyme substrate is attached to the magnetic particle. In one embodiment, the cleavable enzyme substrate is a substrate of an enzyme enriched in a cancer or tumor. In another embodiment, the cleavable enzyme substrate is a substrate of a peptidase enriched in a cancer or tumor. In certain embodiment, the cleavable enzyme substrate is a substrate of Cathepsin G.

In various embodiments, the present invention provides a composition that consists of or consists essentially of or comprises a HDAC inhibitor and a GSK3β inhibitor. In accordance with the present invention, the composition may be used for treating, preventing, reducing the likelihood of having, reducing the severity of and/or slowing the progression of a condition in a subject.

In various embodiments, the HDAC inhibitor is SAHA, TSA, TPX, MS-275, Valproic Acid, or CHAP31, or their functional equivalents, analogs, derivatives or salts, or a combination thereof. In some embodiments, the HDAC inhibitor in the composition is provided in mg HDAC inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the HDAC inhibitor in the composition is provided in µg HDAC inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg, or a combination thereof.

In various embodiments, the GSK3β inhibitor is SB216763, TDZD-8, or Tideglusib (NP-12), or their functional equivalents, analogs, derivatives or salts, or a combination thereof. In some embodiments, the GSK3β inhibitor in the composition is provided in mg GSK3β inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the GSK3β inhibitor in the composition is provided in μg GSK3β inhibitor per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/kg, or a combination thereof.

In various further embodiments, the composition further comprises a cleavable enzyme substrate and a magnetic particle, wherein the HDAC inhibitor and/or the GSK3β inhibitor are attached to the cleavable enzyme substrate and the cleavable enzyme substrate is attached to the magnetic particle. In one embodiment, the cleavable enzyme substrate is a substrate of an enzyme enriched in a cancer or tumor. In another embodiment, the cleavable enzyme substrate is a substrate of a peptidase enriched in a cancer or tumor. In certain embodiment, the cleavable enzyme substrate is a substrate of Cathepsin G.

In certain embodiments, the various compositions described herein further comprise a chemotherapeutic agent. In some embodiments, the chemotherapeutic agent is selected from the group consisting of Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone, and any combination thereof.

In certain embodiments, the pharmaceutical compositions according to the invention are administered to a mammal or human. Preferred pharmaceutical compositions will also exhibit minimal toxicity when administered to a mammal or human. In various embodiments, the pharmaceutical compositions according to the invention are formulated for topical, intravascular, intravenous, intraarterial, intratumoral, intramuscular, subcutaneous, intraperitoneal, intranasal or oral administration.

In various embodiments, the pharmaceutical compositions according to the invention can be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art.

The pharmaceutical compositions according to the invention can be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

In various embodiments, the composition is administered 1-3 times per day, 1-7 times per week, or 1-9 times per month. In various embodiments, the composition is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the composition may be administered once a day (SID/QD), twice a day (BID), three times a day (TID), four times a day (QID), or more, so as to administer an effective amount of the dual inhibitor, the HDAC inhibitor, and/or the GSK3β inhibitor to the subject, where the effective amount is any one or more of the doses described herein.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention can be sterilized by conventional, well-known sterilization techniques. The resulting solutions may be packaged for use or filtered under aseptic conditions and lyophilized, the lyophilized preparation being combined with a sterile solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The pharmaceutical composition according to the invention can also be a bead system for delivering the therapeutic agent to the target cells. For example, pectin/zein hydrogel bead system may be used to deliver Neuregulin-4 or a pharmaceutical equivalent, analog, derivative or a salt thereof, to the target cells in the subject (Yan F. et al., J Clin Invest. 2011 June; 121(6):2242-53).

Kits of the Invention

In various embodiments, the present invention provides a kit for treating, preventing, reducing the severity of and/or slowing the progression of a condition in a subject. The kit consists of or consists essentially of or comprises: a quantity of a dual inhibitor of HDAC and GSK3β; and instructions for using the dual inhibitor to treat, prevent, reduce the likelihood of having, reduce the severity of and/or slow the progression of the condition in the subject.

In some embodiments, the dual inhibitor is a compound of Formula I, Formula II, Formula III, Formula I-1, Formula I-1a, Formula I-1b, Formula I-1c, Formula I-2, Formula I-3, Formula II-1, Formula III-1, Formula IIIb, Formula IIIb-1, Formula IV, Formula V, Formula VI, Formula VII, or a combination thereof.

In various embodiments, the dual inhibitor is conjugated with a particle. In various further embodiments, the dual inhibitor is attached to a cleavable enzyme substrate and the cleavable enzyme substrate is attached to a magnetic particle.

In various embodiments, the present invention provides a kit for treating, preventing, reducing the severity of and/or slowing the progression of a condition in a subject. The kit consists of or consists essentially of or comprises: a quantity of a HDAC inhibitor; a quantity of a GSK3β inhibitor; and instructions for using the HDAC inhibitor and the GSK3β inhibitor to treat, prevent, reduce the likelihood of having, reduce the severity of and/or slow the progression of the condition in the subject.

In various embodiments, the HDAC inhibitor is SAHA, TSA, TPX, MS-275, Valproic Acid, or CHAP31, or their functional equivalents, analogs, derivatives or salts, or a combination thereof. In various embodiments, the GSK3β inhibitor is SB216763, TDZD-8, or Tideglusib (NP-12), or their functional equivalents, analogs, derivatives or salts, or a combination thereof. In various further embodiments, the HDAC inhibitor and/or the GSK3β inhibitor are attached to a cleavable enzyme substrate and the cleavable enzyme substrate is attached to a magnetic particle.

In various further embodiments, the kits according to the present invention further comprise a chemotherapeutic agent and instructions for using the chemotherapeutic agent to treat, prevent, reduce the likelihood of having, reduce the severity of and/or slow the progression of the condition in the subject. In some embodiments, the chemotherapeutic agent in the kit is selected from the group consisting of Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

The kit is an assemblage of materials or components, including at least one of the inventive compositions. The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the pharmaceutical compositions can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Exemplary embodiments of the various aspects disclosed herein can be described by one of more of the following numbered paragraphs:

1. A compound of Formula (IV):

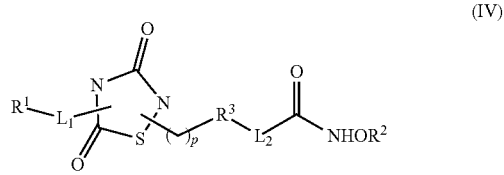

wherein:
$L_1$ and $L_2$ are independently a linker;
$R^1$ is an aromatic moiety, alkyl, acyl, cyclyl or heterocyclyl, each of which can be optionally substituted;
$R^2$ is hydrogen, lower alkyl, cyclyl, heterocyclyl, aryl, or heteroaryl, each of which can be optionally substituted;
$R^3$ is absent or an aromatic moiety, which can be optionally substituted;
p is 0, 1, 2, 3, 4, 5, 6, 7, 8, 9 or 10; and
wherein $-L_1R^1$ is linked to one nitorgen of the thiadiazolidine ring and $—(CH_2)_p—R^3-L_2-C(O)NHOR^2$ is linked to the other nitorgen of the thiadiazolidine ring.

2. The compound of paragraph 1, having the structure of Formula (VI):

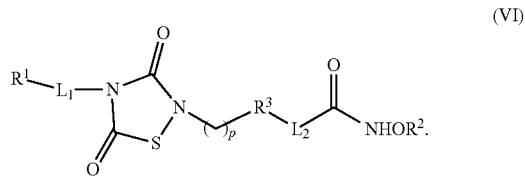

3. The compound of paragraph 1 or 2, having the structure of Formula (I):

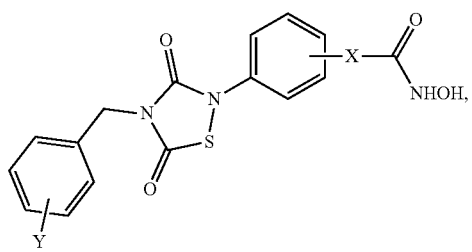

(I)

wherein:
X is a linker group; and
Y is absent or an aromatic substituent.

4. The compound of any of paragraphs 1-3, having the structure of Formula (I-1):

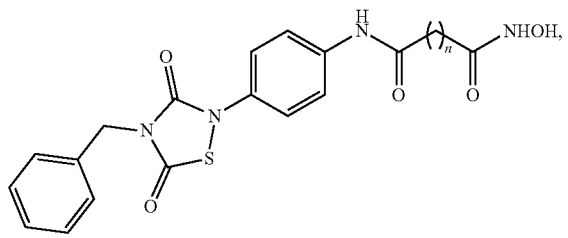

wherein n is an integer from 1 to 12.

5. The compound of any of paragraphs 1-4, wherein the compound is:

6. The compound of paragraph 2, having the structure of Formula (VI):

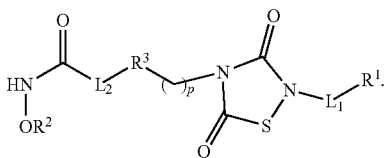

(VII)

7. The compound of any of paragraphs 1, 2, or 6, having the structure of Formula (II):

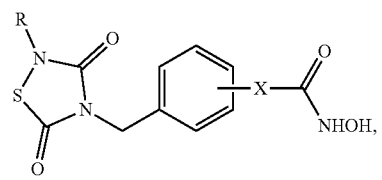

(II)

wherein:
X is a linker group, and R is $-L_1R^1$.

8. The compound of any of paragraphs 1, 2, 6 or 7, having the structure of Formula (II-1):

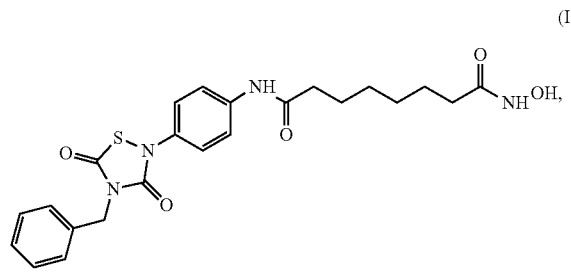

(I-1a)

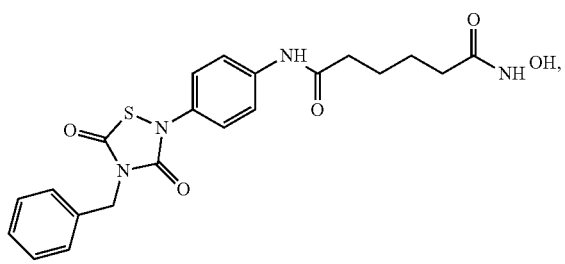

(I-1b)

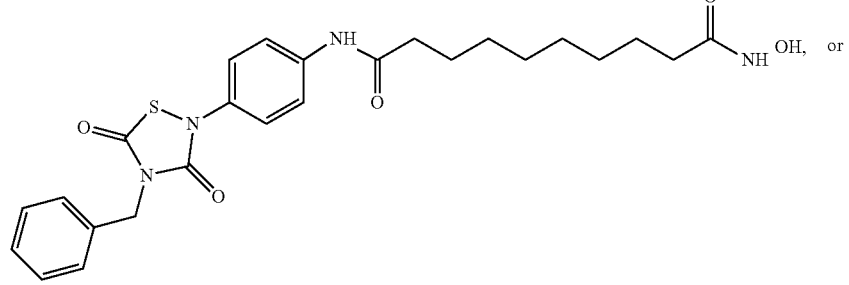

(I-1c)

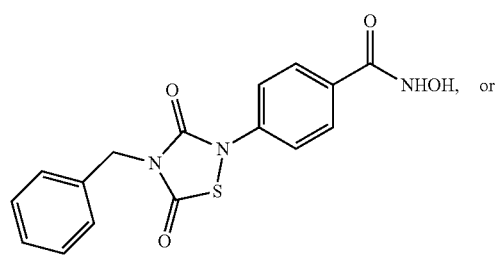

(I-2)

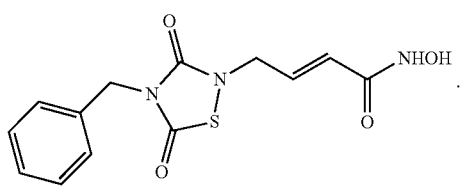

(I-3)

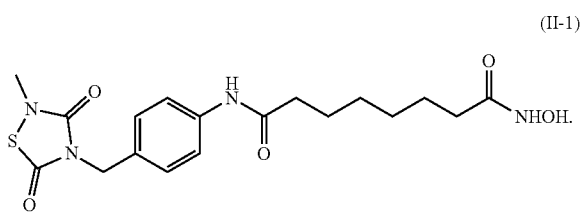
(II-1)

9. A compound of Formula (V):

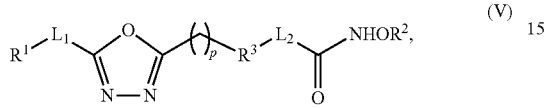
(V)

wherein:
L₁ and L₂ are independently a linker;
R¹ is an aromatic moiety, alkyl, acyl, cyclyl or heterocyclyl, each of which can be optionally substituted;
R² is hydrogen, lower alkyl, cyclyl, heterocyclyl, aryl, or heteroaryl, each of which can be optionally substituted;
R³ is absent or an aromatic moiety, which can be optionally substituted; and
p is 0, 1, 2, 3, 4, 5, 6, 7, 8, 9 or 10.

10. The compound of paragraph 9, having the structure of Formula (III):

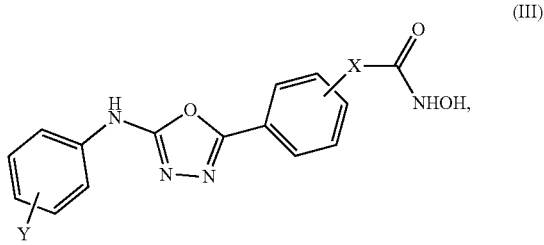
(III)

wherein:
X is a linker group; and
Y is absent or an aromatic substituent.

11. The compound of paragraph 9 or 10, having the structure of Formula (III-1):

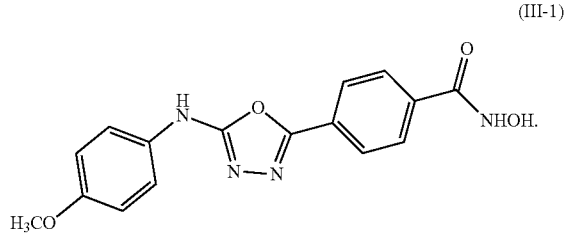
(III-1)

12. The compound of paragraph 9, having the structure of Formula (IIIb):

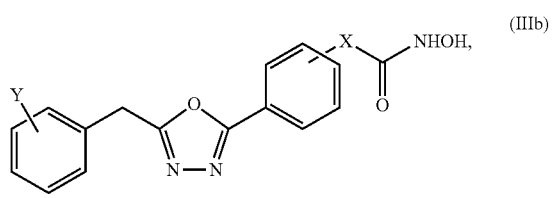
(IIIb)

wherein:
X is a linker group; and
Y is absent or an aromatic substituent.

13. The compound of paragraph 9 or 12, wherein the compound is of Formula (IIIb-1):

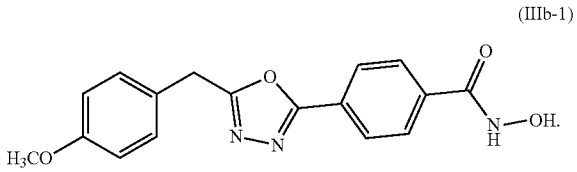 [SMILES: COc1ccc(Cc2nnc(-c3ccc(C(=O)NO)cc3)o2)cc1]
(IIIb-1)

14. The compound of any of paragraphs 1-13, wherein the compound is linked to a particle.
15. The compound of paragraph 14, wherein the particle is a magnetic particle.
16. The compound of paragraph 14 or 15, wherein the compound is linked to a particle via a linker comprising a cleavable linking group.
17. The compound of paragraph 16, wherein the cleavable linking group is cleaved by an enzyme.
18. The compound of paragraph 16 or 17, wherein the cleavable linking group is cleaved by an enzyme enriched in a cancer or tumor.
19. The compound of any of paragraphs 16-18, wherein the cleavable linking group is cleaved by a peptidase enriched in a cancer or tumor.
20. The compound of any of paragraphs 16-19, wherein the cleavable linking group is a cleavable substrate of Cathepsin G.
21. A composition comprising a dual inhibitor of HDAC and GSK3p.
22. The composition of paragraph 21, wherein the dual inhibitor is a compound of anyone of paragraphs 1-20.
23. The composition of paragraph 21 or 22, further comprising a pharmaceutically acceptable carrier or excipient.
24. The composition of any of paragraphs 21-23, wherein the composition is formulated for topical, intravascular, intravenous, intraarterial, intratumoral, intramuscular, subcutaneous, intraperitoneal, intranasal or oral administration.
25. The composition of any of paragraphs 21-24, wherein the composition further comprises an anti-cancer therapeutic agent.
26. The composition of paragraph 25, wherein the anti-cancer therapeutic agent is a chemotherapeutic agent.
27. A method of treating, preventing, reducing the likelihood of having, reducing the severity of and/or slowing the progression of a condition in a subject, comprising: administering a therapeutically effective amount of a dual inhibitor of HDAC and GSK3β to the subject, thereby treating, preventing, reducing the likelihood of having, reducing the severity of and/or slowing the progression of the condition in the subject.

28. The method of paragraph 27, wherein the condition is cancer or tumor.

29. The method of paragraph 27 or 28, wherein the condition is pancreatic cancer.

30. The method of any of paragraphs 27-29, wherein the subject is a human.

31. The method of any of paragraph 27-30, wherein the dual inhibitor is a compound of any of paragraphs 1-20.

32. The method of any of paragraphs 27-32, wherein the dual inhibitor is administered topically, intravascularly, intravenously, intraarterially, intratumorally, intramuscularly, subcutaneously, intraperitoneally, intranasally, or orally.

33. The method of any of paragraphs 27-32, wherein the dual inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof.

34. The method of any of paragraphs 27-32, wherein the dual inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/kg, or a combination thereof.

35. The method of any of paragraphs 27-34, wherein the dual inhibitor is administered about 1-3 times per day, 1-7 times per week, or 1-9 times per month.

36. The method of any of paragraphs 27-35, wherein the dual inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

37. The method of any of paragraphs 27-3627, further comprising administering an additional anti-cancer therapy.

38. The method of paragraph 37, wherein the dual inhibitor and the additional anti-cancer therapy are administered concurrently or sequentially.

39. The method of paragraph 37 or 38, wherein the dual inhibitor is administered before, during or after administering the additional anti-cancer therapy.

40. The method of any of paragraphs 37-39, wherein the additional anti-cancer therapy is selected from the group consisting of surgery, radiation therapy (radiotherapy), biotherapy, immunotherapy, chemotherapy, and any combinations thereof.

41. The method of any of paragraphs 37-40, wherein the additional anti-cancer therapy comprises administering an anti-cancer therapeutic agent to the subject.

42. The method of paragraph 41, wherein the dual inhibitor and the anti-cancer therapeutic agent are provided in one composition.

43. The method of paragraph 41 or 42, wherein the dual inhibitor and the anti-cancer therapeutic agent are provided in separate compositions.

44. The method of any of paragraphs 41-43, wherein the anti-cancer therapeutic agent is a chemotherapeutic agent.

45. The method of any of paragraphs 27-44, wherein the dual inhibitor is linked to a magnetic particle and the method further comprises using a magnetic field to guide the dual inhibitor to a cancer or tumor.

46. A kit for treating, preventing, reducing the likelihood of having, reducing the severity of and/or slowing the progression of a condition in a subject, comprising:
a dual inhibitor of HDAC and GSK3β; and
instructions for using the dual inhibitor to treat, prevent, reduce the likelihood of having, reduce the severity of and/or slow the progression of the condition in the subject.

47. The kit of paragraph 46, wherein the dual inhibitor of HDAC and GSK3β is a compound of any of paragraphs 1-20.

48. The kit of paragraph 46 or 47, further comprising an anti-cancer therapeutic agent.

49. The kit of paragraph 48, wherein the anti-cancer agent is a chemotherapeutic agent.

50. A composition comprising a HDAC inhibitor and a GSK3β inhibitor.

51. The composition of paragraph 50, wherein the HDAC inhibitor is selected from the group consisting of SAHA, TSA, TPX, MS-275, Valproic Acid, or CHAP31, or a functional equivalent, analog, derivative or salt thereof, and any combinations thereof.

52. The composition of paragraph 50 or 51, wherein the GSK3β inhibitor is selected from the group consisting of SB216763, TDZD-8, Tideglusib (NP-12), or a functional equivalent, analog, derivative or salt thereof, and any combinations thereof.

53. The composition of any of paragraphs 50-52, wherein the HDAC inhibitor and/or the GSK3β inhibitor is about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof.

54. The composition of any of paragraphs 50-53, wherein the HDAC inhibitor and/or the GSK3β inhibitor is about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/kg, or a combination thereof.

55. The composition of any of paragraphs 50-54, further comprising a pharmaceutically acceptable excipient or carrier.

56. The composition of any of paragraphs 50-55, wherein the composition is formulated for topical, intravascular, intravenous, intraarterial, intratumoral, intramuscular, subcutaneous, intraperitoneal, intranasal or oral administration.

57. The composition of any of paragraphs 50-56, wherein the composition further comprises an anti-cancer therapeutic agent.

58. The composition of paragraph 57, wherein the anti-cancer therapeutic agent is a chemotherapeutic agent.

59. The composition of paragraph 57 or 58, wherein at least one of the HDAC inhibitor and the GSK3β is conjugated with a particle.

60. The composition of paragraph 59, wherein the particle is a magnetic particle.

61. The composition of paragraph 59 or 60, wherein the HDAC inhibitor and/or the GSK3β is linked to the particle via a linker comprising a cleavable linking group.

62. The composition of paragraph 61 wherein the cleavable linking group is cleaved by an enzyme.

63. The composition of paragraph 61 or 62, wherein the cleavable linking group is cleaved by an enzyme enriched in a cancer or tumor.

64. The composition of any of paragraphs 61-63, wherein the cleavable linking group is cleaved by a peptidase enriched in a cancer or tumor.

65. The composition of any of paragraphs 61-64, wherein the cleavable linking group is a cleavable substrate of Cathepsin G.

66. A method of treating, preventing, reducing the likelihood of having, reducing the severity of and/or slowing the progression of a condition in a subject, comprising:
administering a therapeutically effective amount of a HDAC inhibitor and a GSK3β inhibitor to the subject, thereby treating, preventing, reducing the likelihood of having, reducing the severity of and/or slowing the progression of the condition in the subject.

67. The method of paragraph 66, wherein the condition is cancer or tumor.

68. The method of paragraph 66 or 67, wherein the condition is pancreatic cancer.

69. The method of any of paragraphs 66-68, wherein the subject is a human.

70. The method of any of paragraphs 66-69, wherein the HDAC inhibitor and the GSK3β inhibitor are provided in one composition.

71. The method of any of paragraphs 66-69, wherein the HDAC inhibitor and the GSK3β inhibitor are provided in separate compositions.

72. The method of any of paragraphs 66-71, wherein the HDAC inhibitor and the GSK3β inhibitor are administered concurrently or sequentially.

73. The method of any of paragraphs 66-72, wherein the HDAC inhibitor is administered before, during or after administering the GSK3β inhibitor.

74. The method of any of paragraphs 66-73, wherein the HDAC inhibitor is SAHA, TSA, TPX, MS-275, Valproic Acid, or CHAP31, or a functional equivalent, analog, derivative or salt thereof, or a combination thereof.

75. The method of any of paragraphs 66-74, wherein the GSK3β inhibitor is SB216763, TDZD-8, or Tideglusib (NP-12), or a functional equivalent, analog, derivative or salt thereof, or a combination thereof.

76. The method of any of paragraphs 66-75, wherein the HDAC inhibitor and/or the GSK3β inhibitor is administered topically, intravascularly, intravenously, intraarterially, intratumorally, intramuscularly, subcutaneously, intraperitoneally, intranasally, or orally.

77. The method of any of paragraphs 66-76, wherein the HDAC inhibitor and/or the GSK3β inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof.

78. The method of any of paragraphs 66-76, wherein the HDAC inhibitor and/or the GSK3β inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/kg, or a combination thereof.

79. The method of any of paragraphs 66-78, wherein the HDAC inhibitor and/or the GSK3β inhibitor is administered about 1-3 times per day, 1-7 times per week, or 1-9 times per month.

80. The method of any of paragraphs 66-79, wherein the HDAC inhibitor and/or the GSK3β inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

81. The method of any of paragraphs 66-8027, further comprising administering an additional anti-cancer therapy.

82. The method of paragraph 81, wherein the HDAC inhibitor, the GSK3β inhibitor and the additional anti-cancer therapy are administered concurrently or sequentially.

83. The method of paragraph 81 or 82, wherein the HDAC inhibitor and/or the GSK3β inhibitor is administered before, during or after administering the additional anti-cancer therapy.

84. The method of any of paragraphs 81-83, wherein the additional anti-cancer therapy is selected from the group consisting of surgery, radiation therapy (radiotherapy), biotherapy, immunotherapy, chemotherapy, and any combinations thereof.

85. The method of any of paragraphs 81-84, wherein the additional anti-cancer therapy comprises administering an anti-cancer therapeutic agent to the subject.

86. The method of any of paragraphs 81-85, wherein the HDAC inhibitor, the GSK3β inhibitor and the chemotherapeutic agent are provided in separate compositions.

87. The method of any of paragraphs 81-85, wherein at least two of the HDAC inhibitor, the GSK3β inhibitor and the anti-cancer therapeutic agent are provided in one composition.

88. The method of any of paragraphs 81-85, wherein all three of the HDAC inhibitor, the GSK3β inhibitor and the anti-cancer therapeutic agent are provided in one composition.

89. The method of any of paragraphs 81-88, wherein the anti-cancer therapeutic agent is a chemotherapeutic agent.

90. The method of paragraph 66, wherein at least one of the HDAC inhibitor and the GSK3β is conjugated with a particle.

91. The method of paragraph 90, wherein the particle is a magnetic particle.

92. The method of paragraph 90 or 91, wherein the HDAC inhibitor and/or the GSK3β is linked to the particle via a linker comprising a cleavable linking group.

93. The method of paragraph 92, wherein the cleavable linking group is cleaved by an enzyme.

94. The method of paragraph 92 or 93, wherein the cleavable linking group is cleaved by an enzyme enriched in a cancer or tumor.

95. The method of any of paragraphs 92-94, wherein the cleavable linking group is cleaved by a peptidase enriched in a cancer or tumor.

96. The method of any of paragraphs 92-95, wherein the cleavable linking group is a cleavable substrate of Cathepsin G.

97. The method of any of paragraphs 92-96, wherein at least one of the HDAC inhibitor and the GSK3β is linked to a magnetic particle and the method further comprises using a magnetic field to guide the HDAC inhibitor and/or the GSK3β to a cancer or tumor.

98. A kit for treating, preventing, reducing the likelihood of having, reducing the severity of and/or slowing the progression of a condition in a subject, comprising:
a HDAC inhibitor;
a GSK3β inhibitor; and instructions for using the HDAC inhibitor and the GSK3β inhibitor to treat, prevent, reduce the likelihood of having, reduce the severity of and/or slow the progression of the condition in the subject.

99. The kit of paragraph 98, further comprising an anti-cancer therapeutic agent.

100. The kit of paragraph 98 or 99, wherein the anti-cancer agent is a chemotherapeutic agent.

101. The kit of any of paragraphs 98-101, wherein at least one of the HDAC inhibitor and the GSK3β is conjugated with a particle.

102. The kit of paragraph 101, wherein the particle is a magnetic particle.

103. The kit of paragraph 101 or 102, wherein the HDAC inhibitor and/or the GSK3β is linked to the particle via a linker comprising a cleavable linking group.

104. The kit of paragraph 103, wherein the cleavable linking group is cleaved by an enzyme.

105. The kit of paragraph 103 or 104, wherein the cleavable linking group is cleaved by an enzyme enriched in a cancer or tumor.

106. The kit of any of paragraphs 103-105, wherein the cleavable linking group is cleaved by a peptidase enriched in a cancer or tumor.

107. The kit of any of paragraphs 103-106, wherein the cleavable linking group is a cleavable substrate of Cathepsin G.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Treatment of Pancreatic Cancer by Novel Compounds and Methods that Simultaneously Inhibit Growth Promoting GSKβ and Metastasis and Treatment Resistance Promoting HDAC In various embodiments, the present invention provides cancer treatments combining inhibitors of both GSK3β and HDAC for K-ras mediated neoplasm. A general scheme is shown in FIG. 1 and the experimental results shown in FIGS. 2-7.

The inventors used a mouse model of pancreatic cancer where an oncogene call mutant K-ras is expressed in the pancreas (pdx1-Cre-LSL-Kras). These mice were exposed to cigarette smoke for 6 weeks in smoking chambers. Groups of mice were injected with GSK3β inhibitor TDZD-8 (4 mg/Kg, 3 times per week) and/or HDAC inhibitor Saha (50 mg/Kg; 5 times per week) for 6 weeks.

Figure 2:
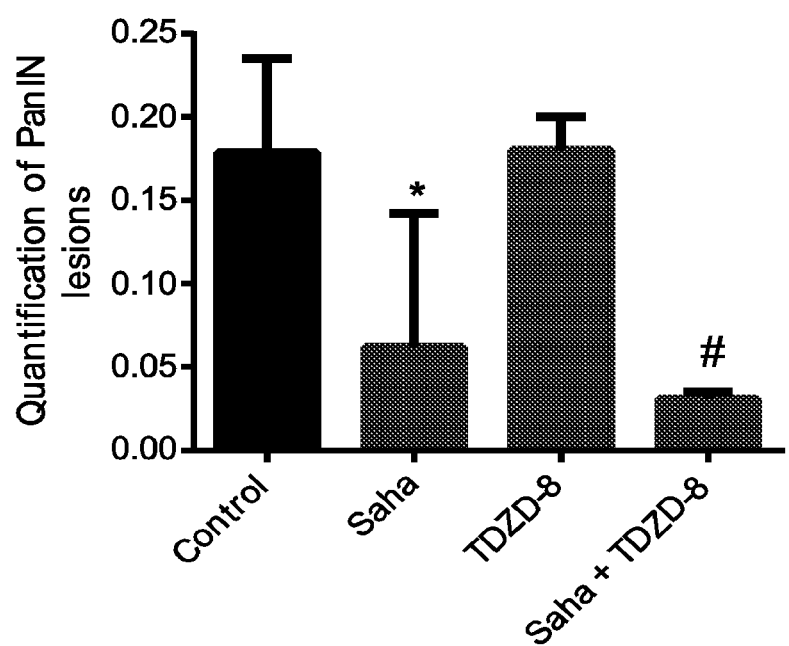
FIG. 2 depicts, in accordance with various embodiments of the invention, effect of HDAC inhibitor Saha (50 mg/Kg) and GSK3β inhibitor (4 mg/Kg) alone and in combination on reducing PanIN lesion formation.
Figure 3:
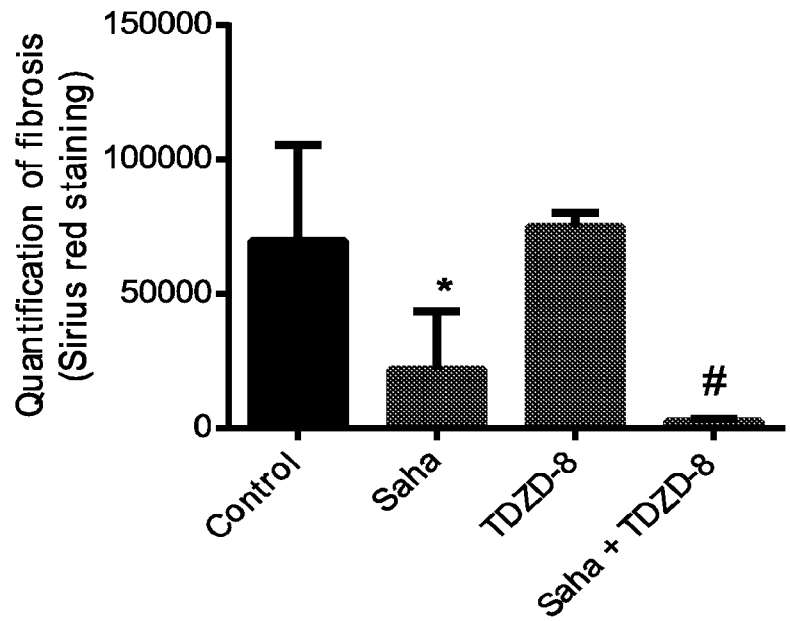
FIG. 3 depicts, in accordance with various embodiments of the invention, effect of HDAC inhibitor Saha (50 mg/Kg) and GSK3β inhibitor (4 mg/Kg) alone and in combination on fibrosis.

The inventors found that animals receiving Saha had significantly decreased formation of early cancer lesions called pancreatic intraepithelial neoplasia (PanIN) compared to a control group; and that the combination of Saha and TDZD-8 significantly increased this effect compared to each compound alone (FIG. 2). The same effect was observed when measuring fibrosis with collagen staining. Fibrosis is a measure of cancer activity. Indeed, the combination of Saha and TDZD-8 synergistically decreased fibrosis (FIG. 3).

Figure 4:
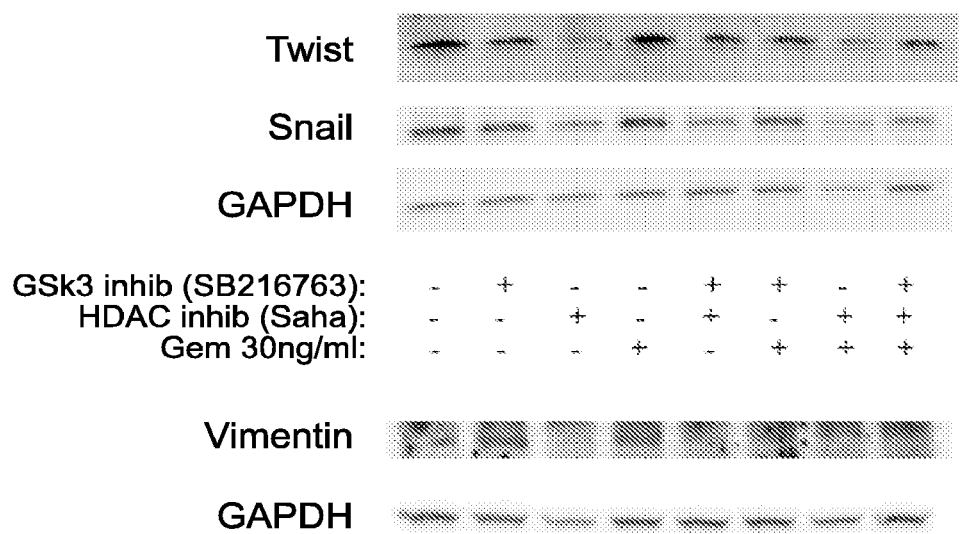
FIG. 4 depicts, in accordance with various embodiments of the invention, effect of HDAC, GSK3β inhibitions combined with gemcitabine on EMT in MIA PaCa-2 pancreatic cancer cells.

Inhibition of GSK3β induces up-regulation of EMT as shown by a measure of vimentin which is an accepted measurement for EMT (FIG. 4). This effect of GSK3β was prevented by the HDAC inhibitor Saha (FIG. 4). Saha also inhibited transcription factors known to regulate EMT such as Twist and Snail. A combination of the two inhibitors with gemcitabine, a chemotherapeutic agent used in pancreatic cancer led to a complete inhibition of the EMT marker vimentin and its transcription factors (FIG. 4).

Figure 5:
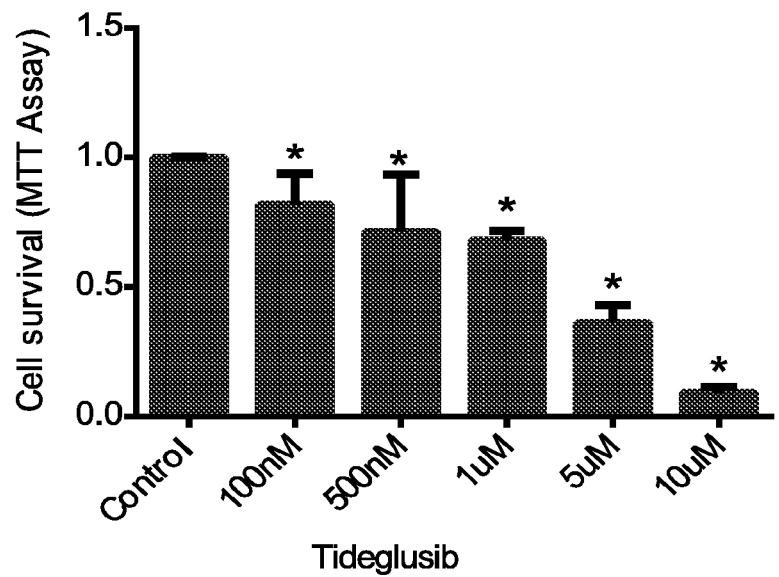
FIG. 5 depicts, in accordance with various embodiments of the invention, dose-dependent effect of GSK3β inhibitor tideglusib on cell survival in pancreatic cancer cells MIA PaCa-2 (* $p<0.05$ compared to control).
Figure 6:
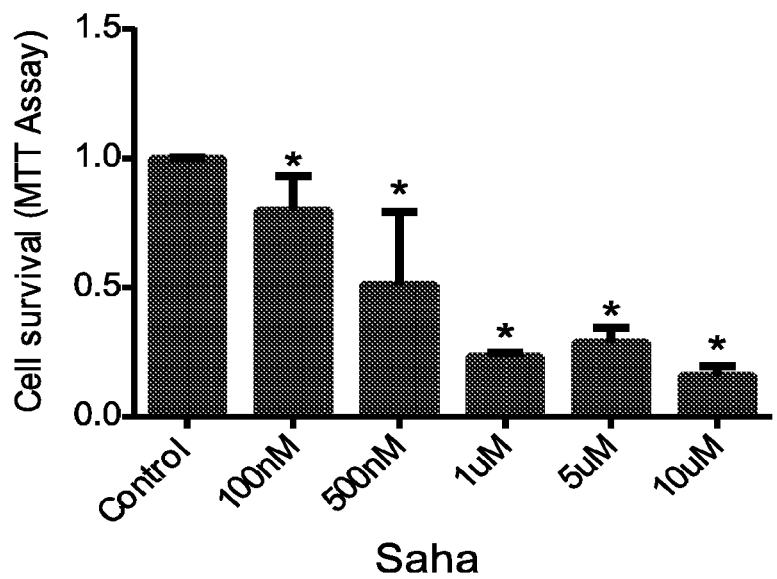
FIG. 6 depicts, in accordance with various embodiments of the invention, dose-dependent effect of HDAC inhibitor Saha on cell survival in pancreatic cancer cells MIA PaCa-2 (* $p<0.05$ compared to control).
Figure 7:
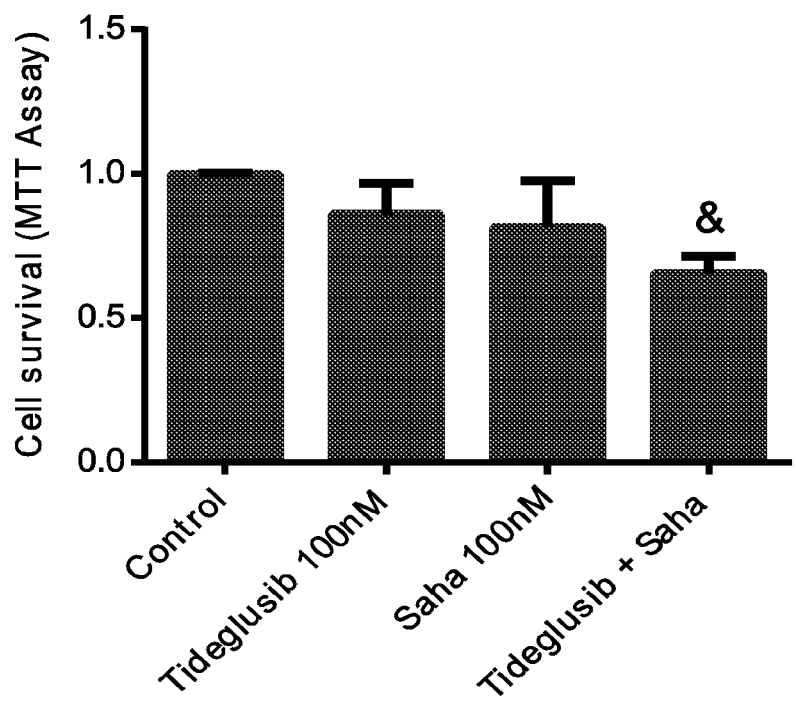
FIG. 7 depicts, in accordance with various embodiments of the invention, effect of combination of GSK3β inhibitor tideglusib and HDAC inhibitor Saha on cell survival in pancreatic cancer cells MIA PaCa-2. (& $p<0.05$ compared to Saha alone).

The combination of low doses of the inhibitors induced synergistic effect on cancer cell survival (FIGS. 5-7). And more importantly, the pro-EMT/metastasis effect of GSK3β inhibition was prevented by the HDAC inhibitor leading to a double beneficial effect by acting synergistically on cell survival and growth and by reversing the side pro-cancer effect of one of the inhibitors.

Example 2: In Vitro and In Vivo Studies on Exemplary Dual Inhibitors

Effect of ALB-185357 on Cell Survival

Figure 13:
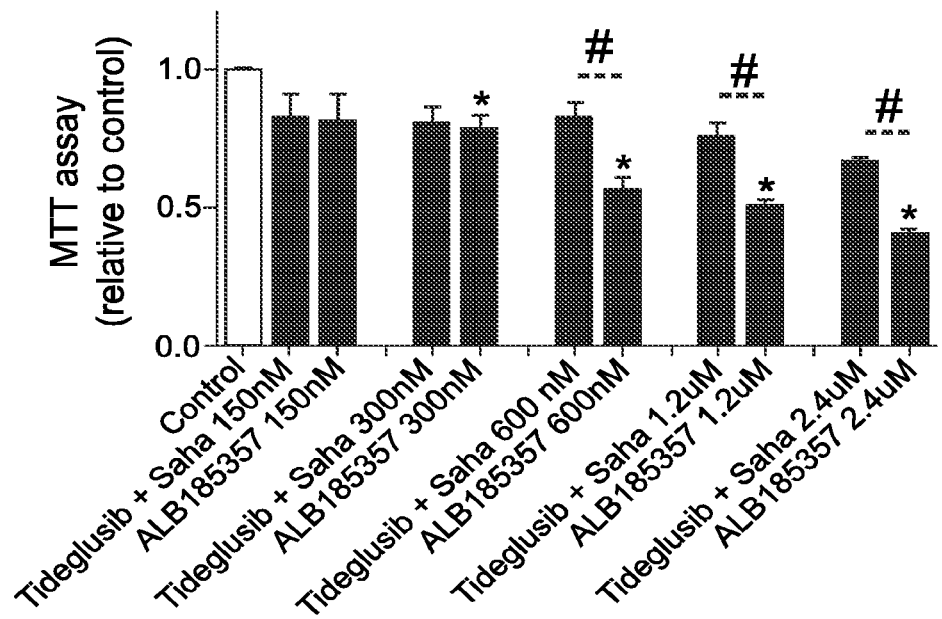
FIG. 13 shows that the compound ALB-185357 dose-dependently decreases cell survival as measured by MTT assay in BxPC-3 pancreatic cancer cell line cultured for 72 h. * Significance compared to control; # significance between tideglusib+saha vs ALB-185357 used at the same concentration, p<0.05.

BxPC-3 pancreatic cancer cell line was cultured in the presence or absence of different doses of a combination of saha and tideglusib or with ALB-185357 for 72 and cell survival measured by MTT assay. The data in FIG. 13 show that the compound ALB-185357 dose-dependently decreased cell survival. The effect of the effect of ALB-185357 was greater than the combination of HDAC inhibitor saha and GSK-3β inhibitor tideglusib. Significance was achieved when using ALB-185357 at 300 nM and its effect on cells survival was bigger than the effect of the combination of saha and tideglusib. As seen from FIGS. 4 and 7, the combination of saha and tideglusib had a synergistic effect on cell death, proliferation and measures of EMT. Thus, the effect of ALB-185357 (a dual inhibitor of HDAC and GSK3β) represents an additional synergism to that observed with the combination of individual agents.

Effect of ALB-185357 on Cell Apoptosis

Figure 14:
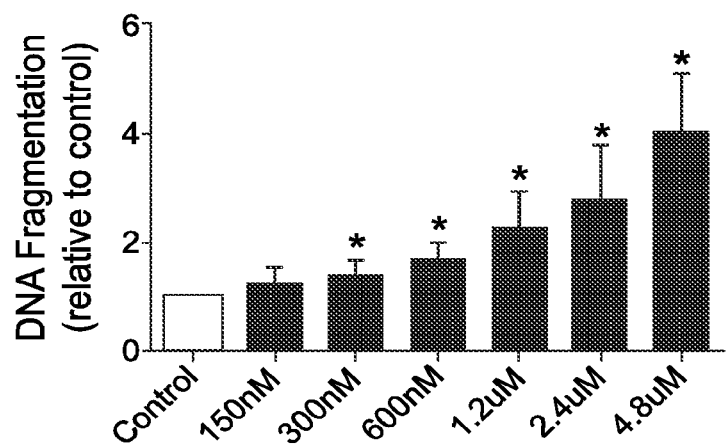
FIG. 14 shows that ALB-185357 dose-dependently increases apoptosis as measured by DNA fragmentation level in MIA PaCa-2 pancreatic cancer cell line. * Significance compared to control, p<0.05.
Figure 15:
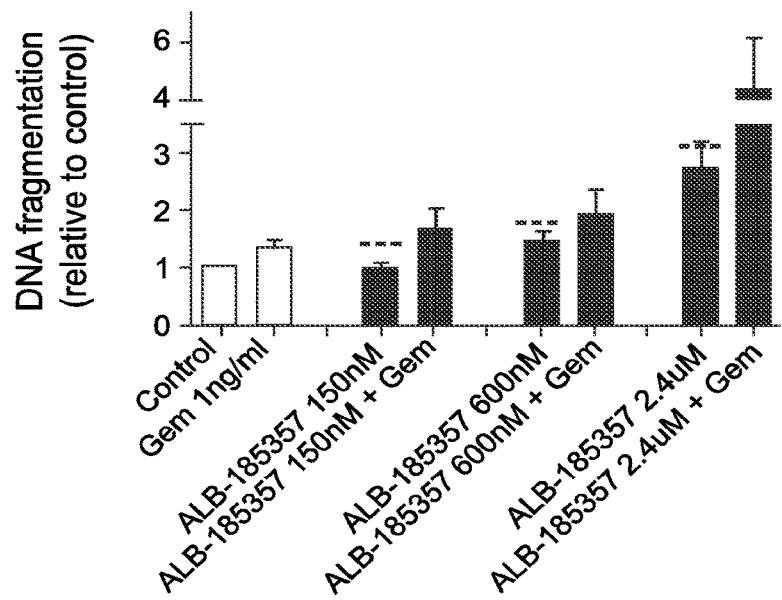
FIG. 15 shows that the combination of ALB-185357 and gemcitabine induces a synergistic effect on inducing apoptosis in MIA PaCa-2 pancreatic cancer cell line. Dashed lane represents the expected additive effect (Significance between expected additive effect and observed effect is achieved at 2.4 uM).

MIA PaCa-2 cells were cultured in the presence or absence of different doses of ALB-185357 for 72 and apoptosis assessed by measuring DNA fragmentation. Results are shown in FIG. 14. As seen from the data in FIG. 14, ALB-185357 dose-dependently increases apoptosis as measured by DNA fragmentation level and significance was achieved at the dose of 300 nM Effect of ALB-185357 and Gemcitabine on Cell Apoptosis MIA PaCa-2 cells were cultured in the presence or absence of different doses of ALB-185357 or gemcitabine at the low dose of 1 ng/ml for 72 and apoptosis assessed by measuring DNA fragmentation. The data in FIG. 15 show that the combination of the ALB-185357 and gemcitabine induced a bigger effect on inducing apoptosis compared to the each drug alone or to the expected additive effect.

Effect of ALB-188540 and ALB-185643 on Cell Survival

Figure 16A:
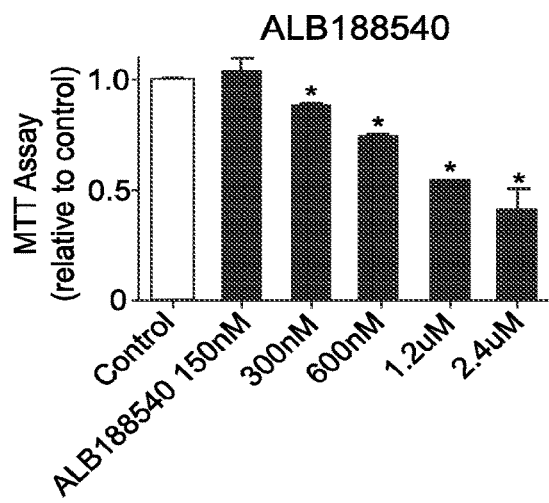
FIGS. 16A and 16B show that compounds ALB-188540 (FIG. 16A) and ALB-185643 (FIG. 16B) show similar effect on survival of BxPC3 cells as the compound ALB-185357. * Significance compared to control, p<0.05.
Figure 16B:
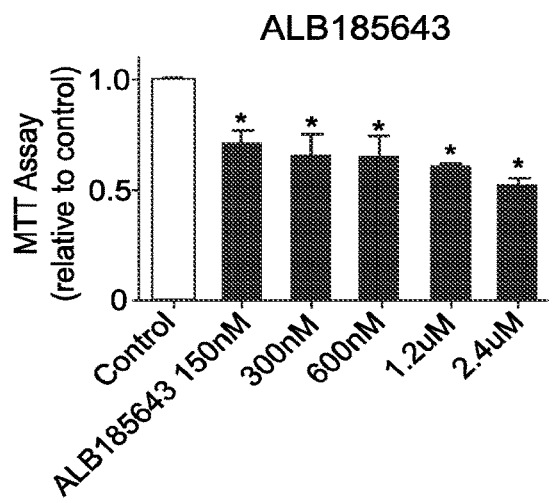

BxPC-3 pancreatic cancer cells were cultured in the presence or absence of different doses of ALB-188540 or ALB-185643 for 72 and cell survival measured by MTT assay. The data in FIGS. 16 and 16B show that compounds ALB-188540 (FIG. 16A) and ALB-185643 (FIG. 16B) had similar effect on survival of BxPC3 cells as the compound ALB-185357.

Figure 17:
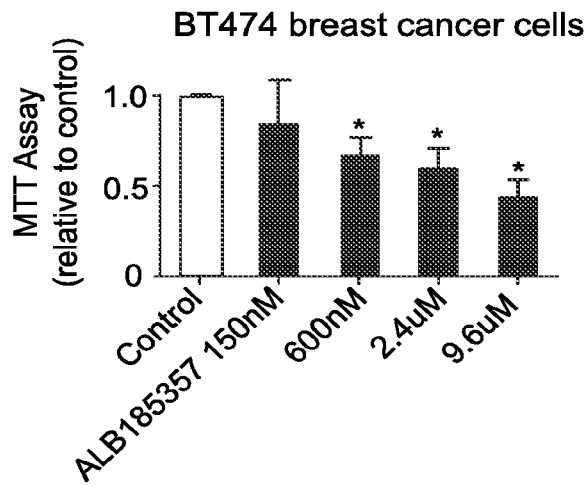
FIG. 17-19 show that compound ALB-185357 dose-dependently decreases cell survival measured by MTT assay and cell numbers in different cancers including in the BT474 breast cancer cells (FIG. 17), hepatocellular carcinoma HepG2 cells (FIG. 18), and Raji lymphoma cells (FIG. 19). * Significance compared to control, p<0.05. This data indicate that ALB-185357 inhibits cells survival of various cancer cell types.
Figure 18:
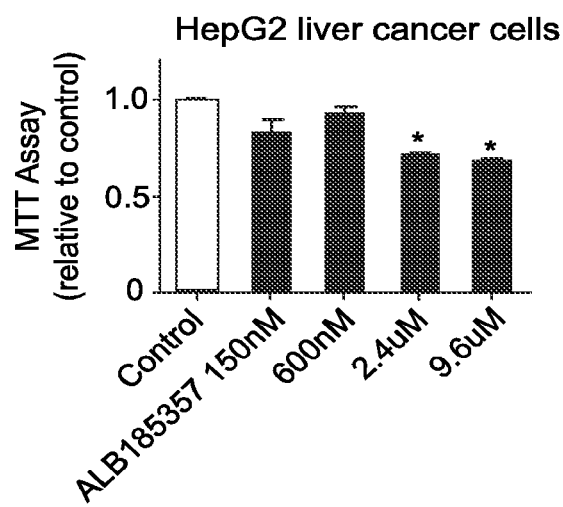
Figure 19:
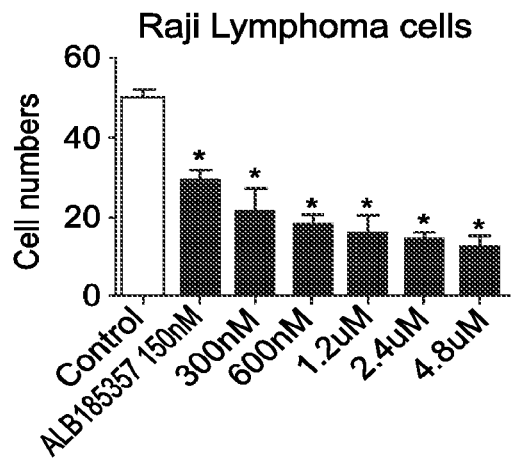

Effect of ALB-185357 on Cell Survival of Different Cancer and Non-Cancer Cell Types Cells were cultured in the presence or absence of different doses of ALB-185357 for 72 and cell survival measured by MTT assay (FIGS. 17 and 18) or by counting cell number (FIG. 19). The results of MTT assay are shown in FIGS. 17 and 18 and results of cell counting are shown in FIG. 19. This data demonstrate that ALB-185357 inhibits cells survival of various cancer cell types.

Figure 20:
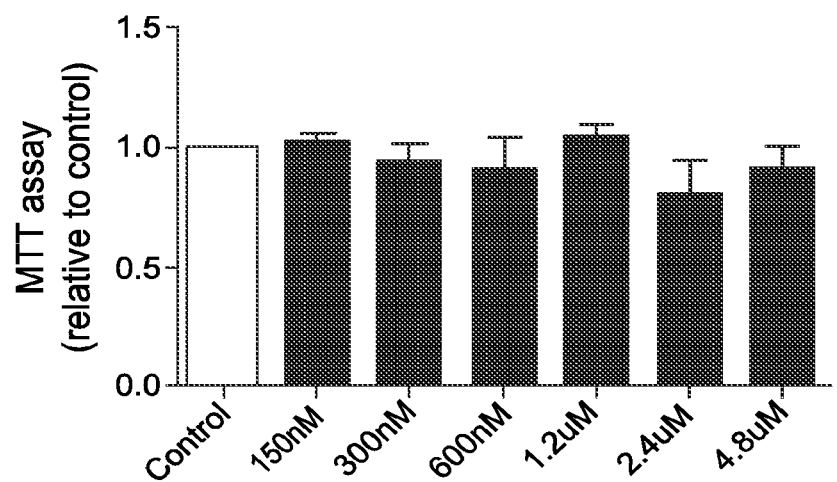
FIG. 20 shows that the compound ALB-185357 does not affect cell survival of normal pancreatic ductal cells. * Significance compared to control, p<0.05.

Cells were cultured in the presence or absence of different doses of ALB-185357 for 72 and cell survival measured by MTT assay. The data in FIG. 20 show that the compound ALB-185357 does not affect cell survival of normal pancreatic ductal cells.

Taken together, the data in FIGS. 17-20 demonstrate that ALB-185357 is highly toxic to cancer cells from different cancer types, but has no toxicity against normal cells.

Figure 21:
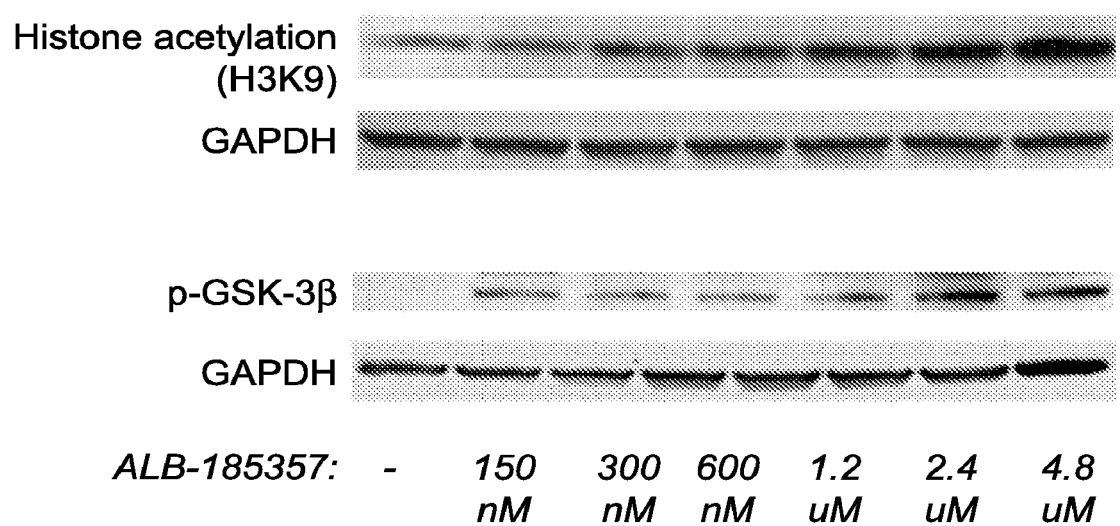
FIG. 21 shows that the compound ALB-185357 dose-dependently up-regulates the predicted targets histone acetylation and GSK-3β phosphorylation/inhibition in MIA PaCa-2 pancreatic cancer cell line.

Effect of ALB-185357 on Histone Acetylation and GSK-3β Phosphorylation/Inhibition Cells were cultured in the presence or absence of different doses of ALB-185357 for 72 and protein levels measured by Western. The data show that the pathways expected to be regulated by ALB-185357 are, indeed, regulated by the drug. As seen in FIG. 21, the compound ALB-185357 dose-dependently up-regulates the predicted targets histone acetylation and GSK-3β phosphorylation/inhibition in MIA PaCa-2 pancreatic cancer cell line.

Figure 22A:
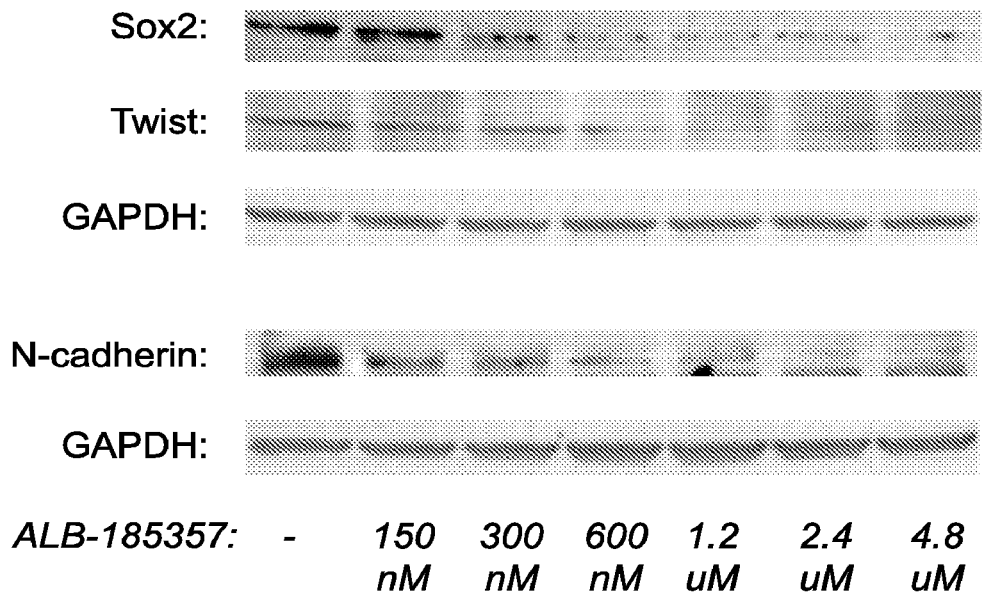
FIGS. 22A and 22B show that the compound ALB-185357 decreases expression of markers of epithelial to mesenchymal transition (N-cadherin and twist), which mediate metastasis, and cancer stemness marker (Sox2), which mediate resistance to treatments (FIG. 22A), and decreases the invasion of MIA PaCa-2 pancreatic cancer cell line (FIG. 22B).
Figure 22B:
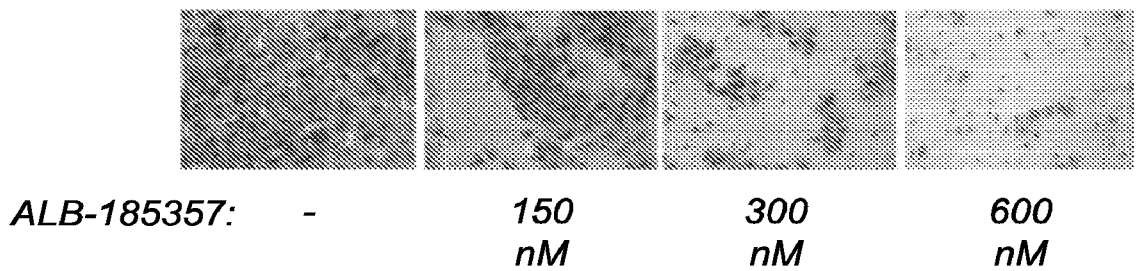

Effect of ALB-185357 on Histone Acetylation and GSK-3β Phosphorylation/Inhibition Cells were cultured in the presence or absence of different doses of ALB-185357 for 72 and protein levels measured by Western (FIG. 22A) and cell invasion measured in Matrigel Invasion Chambers (FIG. 22B). The data in FIG. 22A show that ALB-185357 down-regulates proteins that mediate cell's metastasis and resistance to treatments. The data in FIG. 22B show that the ability of the cancer cells to invade is down-regulated.

In Vivo Effect of ALB-185357 on Survival

Figure 23:
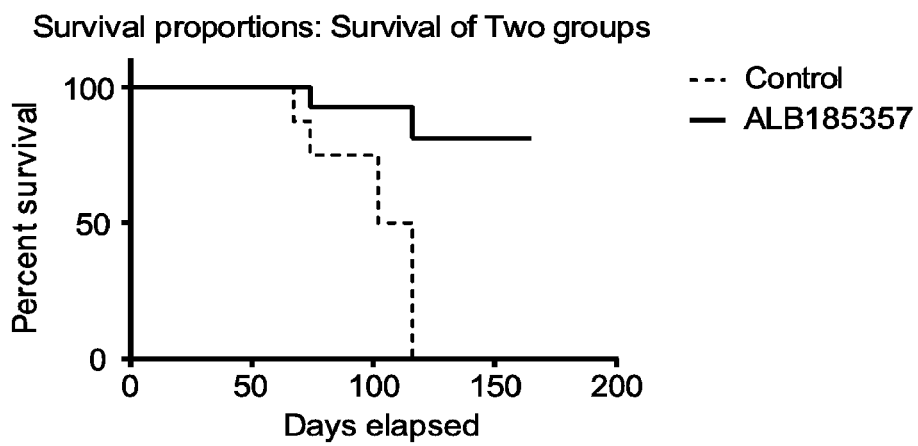
FIG. 23 shows that the compound ALB-185357 significantly increases mice survival by at least 50%.

KPC mice, which have Kras and p53 mutations and spontaneously develop pancreatic adenocarcinoma, were ip injected 3 times per week with 5 mg/Kg of ALB185357 from age 8 weeks until death. As seen from FIG. 23, the compound ALB-185357 improves survival of animals with advance pancreatic cancer.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A compound of Formula (IV):

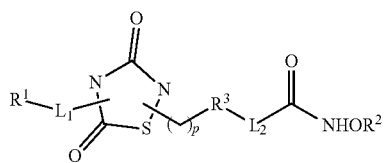

(IV)

wherein:

$L_1$ and $L_2$ are independently a linker;

$R^1$ is an aromatic moiety, alkyl, acyl, cyclyl or heterocyclyl, each of which can be optionally substituted;

$R^2$ is hydrogen, lower alkyl, cyclyl, heterocyclyl, aryl, or heteroaryl, each of which can be optionally substituted;

$R^3$ is absent or an aromatic moiety, which can be optionally substituted;

p is 0, 1, 2, 3, 4, 5, 6, 7, 8, 9 or 10; and wherein $—L_1R^1$ is linked to one nitrogen of the thiadiazolidine ring and $—(CH_2)_p—R^3-L_2-C(O)NHOR^2$ is linked to the other nitrogen of the thiadiazolidine ring.

2. The compound of claim 1, having the structure of Formula (VI):

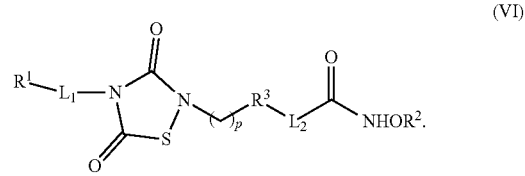

(VI)

3. The compound of claim 2, having the structure of Formula (I):

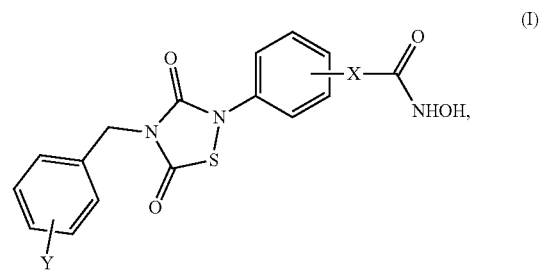

(I)

wherein:

X is a linker group; and

Y is absent or an aromatic substituent.

4. The compound of claim 3, having the structure of Formula (I-1):

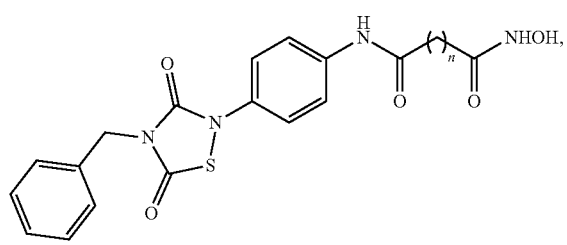

wherein n is an integer from 1 to 12.

5. The compound of claim 1, wherein the compound is:

(I-1a)

(I-1b)

(I-1c)

(I-2)

(I-3)

6. The compound of claim 1, having the structure of Formula (VI):

(VII)

7. The compound of claim 6, having the structure of Formula (II):

(II)

wherein:
X is a linker group, and R is -L₁R¹.

8. The compound of claim 7, having the structure of Formula (II-1):

(II-1)

9. A composition comprising a dual inhibitor of HDAC and GSK3β, wherein the dual inhibitor is a compound of claim 1.

10. The composition of claim 9, further comprising a pharmaceutically acceptable carrier or excipient.

11. The composition of claim 9, wherein the composition is formulated for topical, intravascular, intravenous, intraarterial, intratumoral, intramuscular, subcutaneous, intraperitoneal, intranasal or oral administration.

12. The composition of claim 9, wherein the composition further comprises an anti-cancer therapeutic agent.

13. The composition of claim 12, wherein the anti-cancer therapeutic agent is a chemotherapeutic agent.

* * * * *